US008318898B2

(12) United States Patent
Fasel et al.

(10) Patent No.: US 8,318,898 B2
(45) Date of Patent: Nov. 27, 2012

(54) SYNTHETIC PEPTIDES FOR USE AS INHIBITORS OF NEUROTRANSMITTER SECRETION AND AS INDUCERS OF CELLULAR RELAXATION

(75) Inventors: Nicolas Fasel, Paudex (CH); Amal Kündig, Lausanne (CH)

(73) Assignee: Universite de Lausanne, Lausanne (CH)

( * ) Notice: Subject to any disclaimer, the term of this patent is extended or adjusted under 35 U.S.C. 154(b) by 692 days.

(21) Appl. No.: 12/158,775

(22) PCT Filed: Dec. 22, 2006

(86) PCT No.: PCT/EP2006/012501
§ 371 (c)(1),
(2), (4) Date: Oct. 17, 2008

(87) PCT Pub. No.: WO2007/071448
PCT Pub. Date: Jun. 28, 2007

(65) Prior Publication Data
US 2009/0226387 A1    Sep. 10, 2009

Related U.S. Application Data

(60) Provisional application No. 60/753,607, filed on Dec. 23, 2005.

(51) Int. Cl.
C07K 14/00      (2006.01)
A61K 8/02       (2006.01)
(52) U.S. Cl. ............. 530/350; 514/536; 514/78.01; 514/78.03; 514/78.06; 424/400; 601/17
(58) Field of Classification Search .............. None
See application file for complete search history.

(56) References Cited

U.S. PATENT DOCUMENTS

| | | | |
|---|---|---|---|
| 3,817,837 A | 6/1974 | Rubenstein et al. | |
| 3,850,752 A | 11/1974 | Schuurs et al. | |
| 3,939,350 A | 2/1976 | Kronick et al. | |
| 3,996,345 A | 12/1976 | Ullman et al. | |
| 4,277,437 A | 7/1981 | Maggio | |
| 5,424,398 A | 6/1995 | Middeldorp et al. | |
| 6,183,759 B1 | 2/2001 | Hattori et al. | |
| 6,358,929 B1 | 3/2002 | Mahe et al. | |
| 6,551,795 B1 * | 4/2003 | Rubenfield et al. | 435/69.1 |
| 6,620,419 B1 | 9/2003 | Lintner | |
| 6,794,362 B1 | 9/2004 | Sandberg et al. | |
| 6,821,524 B2 | 11/2004 | Marini | |
| 6,946,436 B2 | 9/2005 | Wakamatsu et al. | |
| 7,514,224 B2 * | 4/2009 | Lu et al. | 435/7.1 |
| 2002/0074461 A1 | 6/2002 | Gombert | |
| 2004/0123343 A1 | 6/2004 | La Rosa et al. | |
| 2005/0106695 A1 | 5/2005 | Bonny | |
| 2005/0175636 A1 | 8/2005 | Donovan | |
| 2005/0281816 A1 | 12/2005 | Lamping et al. | |
| 2007/0166281 A1 * | 7/2007 | Kosak | 424/85.1 |

FOREIGN PATENT DOCUMENTS

| | | |
|---|---|---|
| EP | 1180524 | 2/2002 |
| WO | WO-97/05265 | 2/1997 |
| WO | WO-97/34620 | 9/1997 |
| WO | WO/99/55899 | * 11/1999 |
| WO | WO00/69897 | * 11/2000 |
| WO | WO02/18572 | 3/2002 |
| WO | WO2006/108052 | 10/2006 |

OTHER PUBLICATIONS

Ahsan et al., "Sucrose cocoate, a component of cosmetic preparations, enhances nasal and ocular peptide absorption," *Int. J. Pharm.*, 251:195-203 (2003).
Anwer et al., "Backbone modifications in cyclic peptides. Conformational analysis of a cyclic pseudopentapeptide containing a thiomethylene ether amide bond replacement," *Int. J. Pept. Protein Res.*, 36:392-9 (1990).
Avila et al., "Differential regulation of nicotinic acetylcholine receptors in PC12 cells by nicotine and nerve growth factor," *Mol. Pharmacol.*, 64:974-86 (2003).
Barany et al., "Solid-phase peptide synthesis: a silver anniversary report," *Int. J. Pept. Protein Res.*, 30:705-39 (1987).
Better al., "*Escherichia coli* secretion of an active chimeric antibody fragment," *Science*, 240:1041-3 (1988).
Blanes-Mira et al., "A synthetic hexapeptide (Argireline) with antiwrinkle activity," *Int. J. Cosmetic Sci.*, 24:303-10 (2002).
Boehncke, "The SCID-hu xenogeneic transplantation model: complex but telling," *Arch. Dermatol. Res.*, 291:367-73 (1999).
Brady et al., "Drug design. Reflections on a peptide," *Nature*, 368:692-3 (1994).
Burgoyne et al., "Analysis of regulated exocytosis in adrenal chromaffin cells: insights into NSF/SNAP/SNARE function," *Bioessays*, 20:328-35 (1998).
Burgoyne et al., "Ca2+ and secretory-vesicle dynamics," *Trends Neurosci.*, 18:191-6 (1995).
Burgoyne et al., "Characterization of proteins that regulate calcium-dependent exocytosis in adrenal chromaffin cells," *Ann. NY Acad. Sci.*, 710:333-46 (1994).
Chen et al., "Modulation of intracellular calcium transients and dopamine release by neuropeptide Y in PC-12 cells," *Am. J. Physiol.*, 266:C784-93 (1994).
Dietz et al., "Delivery of bioactive molecules into the cell: the Trojan horse approach," *Mol. Cell Neurosci.*, 27:85-131 (2004).
Dreher et al., "Comparison of cutaneous bioavailability of cosmetic preparations containing caffeine or alpha-tocopherol applied on human skin models or human skin ex vivo at finite doses," *Skin Pharmacol. Appl. Skin Physiol.*, 15 Suppl 1:40-58 (2002).
Dubois et al., "Evidence that furin is an authentic transforming growth factor β-1 converting enzyme," *Am. J. Pathol.*, 158:305-16 (2001).

(Continued)

*Primary Examiner* — Daniel E Kolker
*Assistant Examiner* — Stacey MacFarlane
(74) *Attorney, Agent, or Firm* — McCarter & English, LLP; Cristin H. Cowles; Marcie B. Clarke

(57) ABSTRACT

The present invention describes materials and methods related to synthetic peptides which block the secretion of neurotransmitters and induce muscle relaxation, and use of said peptides as inhibitors of neurotransmitter secretion and muscle contraction, and as inducers of muscle relaxation.

38 Claims, 13 Drawing Sheets

OTHER PUBLICATIONS

Duval et al., "The use of reconstructed human skin to evaluate UV-induced modifications and sunscreen efficac ," *Exp. Dermatol.*, 12 Suppl 2:64-70 2003.

Elliott et al., "Intercellular trafficking and protein delivery by a herpesvirus structural protein," *Cell*, 88:223-33 (1997).

Engelhard et al., "The insect tracheal system: a conduit for the systemic spread of *Autographa californica* M nuclear polyhedrosis virus," *Proc. Natl. Acad. Sci. USA*, 91:3224-7 (1994).

Greene et al., "Establishment of a noradrenergic clonal line of rat adrenal pheochromocytoma cells which respond to nerve growth factor," *Proc. Natl. Acad. Sci. USA*, 73:2424-8 (1976).

Greene et al., "Release of (3H)norepinephrine from a clonal line of pheochromocytoma cells (PC12) by nicotinic cholinergic stimulation," *Brain Res.*, 138:521-8 (1977).

Greene et al., "Release of norepinephrine from neurons in dissociated cell cultures of chick sympathetic ganglia via stimulation of nicotinic and muscarinic acetylcholine receptors," *J. Neurochem.*, 30:579-86 (1978).

Greene et al., "Release, storage and uptake of catecholamines by a clonal cell line of nerve growth factor (NGF) responsive pheochromocytoma cells," *Brain Res.*, 129:247-63 (1977).

Greene et al., "Short-term regulation of catecholamine biosynthesis in a nerve growth factor responsive clonal line of rat pheochromocytoma cells," *J. Neurochem.*, 30:549-55 (1978).

Greene et al., "Synthesis, storage and release of acetylcholine by a noradrenergic pheochromocytoma cell line," *Nature*, 268:349-51 (1977).

Gu et al., "In vitro evaluation of concurrent use of commercially available insect repellent and sunscreen protection," *Br. J. Dermatol.*, 152:1263-7 (2005).

Guichard et al., "Partially modified retro-inverso pseudopeptides as non-natural ligands for the human class I histocompatibility molecule HLA-A2," *J. Med. Chem.*, 39:2030-9 (1996).

Gutierrez et al., "A peptide that mimics the C-terminal sequence of SNAP-25 inhibits secretory vesicle docking in chromaffin cells," *J. Biol. Chem.*, 272:2634-9 (1997).

Harris et al., "Silicone rubber substrata: a new wrinkle in the study of cell locomotion," *Science*, 208:177-9 (1980).

Hashimoto et al., "Blockage of nerve growth factor action in PC12h cells by staurosporine, a potent protein kinase inhibitor," *J. Neurochem.*, 53:1675-85 (1989).

Hashimoto et al., "Staurosporine-induced neurite outgrowth in PC12h cells," *Exp. Cell Res.*, 184:351-9 (1989).

Hinz et al., "Alpha-smooth muscle actin expression upregulates fibroblast contractile activity," *Mol. Biol. Cell.*, 12:2730-41 (2001).

International Preliminary Report on Patentability for corresponding International Application No. PCT/EP2006/012501 (Jun. 24, 2008).

International Search Report and Written Opinion for corresponding International Application No. PCT/EP2006/012501 (Aug. 29, 2007).

Jackson et al., "Heat shock induces the release of fibroblast growth factor 1 from NIH 3T3 cells," *Proc. Natl. Acad. Sci. USA*, 89:10691-5 (1992).

Jameson et al., "A rationally designed CD4 analogue inhibits experimental allergic encephalomyelitis," *Nature*, 368:744-6 (1994).

Jin et al., "Transduction of human catalase mediated by an HIV-1 TAT protein basic domain and arginine-rich peptides into mammalian cells," *Free Radic. Biol. Med.*, 31:1509-19 (2001).

Kanga et al., "Skin care delivery systems," *Happi Magazine*, pp. 47-54 (Jan. 2004).

Kelemen et al., "Selective in vivo inhibition of mitogen-activated protein kinase activation using cell-permeable peptides," *J. Biol. Chem.*, 277:8741-8 (2002).

Lupo, "Cosmeceutical peptides," *Dermatologic Surgery: Official Publication for American Society for Dermatologic Surgery*, 31:832-6 (2005).

Martin et al., "PC12 cells as a model for studies of regulated secretion in neuronal and endocrine cells," *Methods Cell Biol.*, 71:267-86 (2003).

Merrifield, "Solid phase synthesis," *Science*, 232:341-7 (1986).

Montecucco et al., "Botulinal neurotoxins: revival of an old killer," *Curr. Opin. Pharmacol.*, 5:274-9 (2005).

Montecucco et al., "Tetanus and botulism neurotoxins: a new group of zinc proteases," *Trends Biochem. Sci.*, 18:324-7 (1993).

Park et al., "9-polylysine protein transduction domain: enhanced penetration efficiency of superoxide dismutase into mammalian cells and skin," *Mol. Cells*, 13:202-8 (2002).

Rivera-Baeza et al., "Backbone-to-backbone cyclized and linear pseudopeptide analogs of substance P as ligands to the substance P receptor from rat brain," *Neuropeptides*, 30:327-33 (1996).

Sugrue et al., "Furin cleavage of the respiratory syncytial virus fusion protein is not a requirement for its transport to the surface of virus-infected cells," *J. Gen. Virol.*, 82:1375-86 (2001).

Tam et al., "SN2 deprotection of synthetic peptides with a low concentration of HF in dimethyl sulfide: evidence and application in peptide synthesis," *J. Am. Chem. Soc.*, 105:6442-55 (1983).

Tischler et al., "Morphologic and cytochemical properties of a clonal line of rat adrenal pheochromocytoma cells which respond to nerve growth factor," *Lab Invest.*, 39:77-89 (1978).

Wang et al., "Shedding of membrane type matrix metalloproteinase 5 by a furin-type convertase: a potential mechanism for down-regulation," *J. Biol. Chem.*, 276:35953-60 (2001).

Wu et al., "Structural features of the kringle domain determine the intracellular degradation of under-gamma-carboxylated prothrombin: studies of chimeric rat/human prothrombin," *Proc. Natl. Acad. Sci. USA*, 94:13654-60 (1997).

\* cited by examiner

FIG. 1A

| Peptide SEQ ID NO: | Full name | Sequence | Length |
|---|---|---|---|
| 1 | L-Tat-ESUP-A | GYGRKKRRQRRRGSNKTRIDEANQRATKMLGSG | 33 mer |
| 2 | L-Tat-Argireline | YGRKKRRQRRRQGAGGEEMQRR-NH$_2$ | 22 mer |
| 3 | L-Tat | GYGRKKRRQRRRG | 13 mer |
| 4 | L-Tat 49-86 | GRKKRRQRRRAHQNSQTHQASLSKQPTSQPRGDPTGKEG | 39 mer |
| 5 | 9R-L | GYGRRRRRRRRRG | 13 mer |
| 6 | 9K-L | GYGKKKKKKKKKG | 13 mer |
| 7 | MRP$_{ED}$ | KKKKKFSFKKPFKLSGLSFKRNRK | 24 mer |
| 8 | 3DMRP$_{ED}$ | KKKKKFDFKKPFKLDGLDFKRNRK | 24 mer |
| 9 | L-Tat-MRP$_{ED}$ | GYGRKKRRQRRRG-KKKKKFSFKKPFKLSGLSFKRNRK | 37 mer |
| 10 | L-Tat-3DMRP$_{ED}$ | GYGRKKRRQRRRG-KKKKKFDFKKPFKLDGLDFKRNRK | 37 mer |
| 11 | 9R-L-/Ac-am | Acetyl-GYGRRRRRRRRRG-NH$_2$ | 13 mer |
| 12 | D-Tat | GYGRKKRRQRRRG | 13 mer |
| 13 | 9R-D | GYGRRRRRRRRRG | 13 mer |

FIG. 1B

| 14 | 9Rrev-D | GRRRRRRRRRGYG | 13 mer |
|---|---|---|---|
| 15 | 9R-D/Ac-am (D-9Rac/am) | Acetyl-GYGRRRRRRRRRG-NH₂ | 13-mer |
| 16 | 3R | GYGRRRG | 7 mer |
| 17 | 4R | GYGRRRRG | 8 mer |
| 18 | 5R | GYGRRRRRG | 9 mer |
| 19 | 6R | GYGRRRRRRG | 10 mer |
| 20 | 7R | GYGRRRRRRRG | 11 mer |
| 21 | 8R | GYGRRRRRRRRG | 12 mer |
| 22 | 9R-MRP | GYGRRRRRRRRRGKKKKKKFSFKKPFKLSGLSFKRNRK | 38 mer |
| 23 | 9R-D Argireline | GYGRRRRRRRRRGEEMQRR-NH₂ | 19 mer |

FIG. 6A

Effect of Ion Chelators on intracellular Furin Activity In Crude PC12-ES cells

Legend:
- ♦ 20µg crude+Boc-RVRR-AMC
- ☐ 20µg crude+Boc-RVRR-AMC+EDTA 50mM
- ✶ 20µg crude+Boc-RVRR-AMC+EDTA 10mM
- — 20µg crude+Boc-RVRR-AMC+EGTA 50mM
- ■ 20µg crude+Boc-RVRR-AMC+EGTA 10mM X-axis: Time (min)
Y-axis: Fluorescence units

FIG. 6B

Effect of 50µM d-RVKR-CMK on intracellular Furin Activity In Crude PC12-ES cells

Legend:
- ♦ 20µg crude+Boc-RVRR-AMC
- ■ 20µg crude+Boc-RVRR-AMC+d-RVKR-CMK 50µM

X-axis: Time (min)
Y-axis: Fluorescence units

NO PEPTIDE    10 μM    100 μM

A.

B.

SYNTHETIC PEPTIDES FOR USE AS INHIBITORS OF NEUROTRANSMITTER SECRETION AND AS INDUCERS OF CELLULAR RELAXATION

This application claims the priority benefit of U.S. Provisional Patent Application No. 60/753,607, filed Dec. 23, 2005, herein incorporated by reference.

SEQUENCE LISTING

The instant application contains a Sequence Listing which has been submitted in ASCII format via EFS-Web and is hereby incorporated by reference in its entirety. Said ASCII copy, created on Aug. 26, 2011, is named SeqList and is 8.75 kilobytes in size.

FIELD OF THE INVENTION

The present invention describes materials and methods related to synthetic peptides which block the secretion of neurotransmitters and induce cellular relaxation and use of said peptides as inhibitors of neurotransmitter secretion and muscle contraction and as inducers of muscle relaxation.

BACKGROUND

Wrinkles and fine lines are signs of aging. Anti-wrinkle creams make up a sizeable proportion of products intended to keep the skin youthful as long as possible. For many years, wrinkles and fine lines have been treated by moisturizing the skin, improving skin renewal, preventing degeneration of elastic fibers or promoting the synthesis of collagen.

In the category of cosmetic treatments to smooth human skin Restylane and Perlane (Q-Med, Uppsala, Sweden), which are genetically engineered hyaluronic acid derivatives, serve as a sort of collagen supplement. Collagen, the most abundant protein in the body, is an elastic polymer that makes skin firm and durable. As people age, collagen is lost from the dermal, or deeper skin layer, rendering skin more wrinkly and stiff. Retinoic acid (vitamin A) is an effective non-injection treatment for the skin, and is often used in medical treatments as well as in over-the-counter creams and lotions.

The numerous anti-aging and wrinkle creams on the cosmetic market improve the skin temporarily, but often only treat the outermost layer of skin, the epidermis. Collagen glands lie in the dermis, and so are unaffected by these creams. To circumvent this problem, alternative approaches are available. DHEA (dehydroepiandro-sterone) is a product secreted by the human adrenal glands whose serum concentration declines with aging. DHEA has indirect endocrine and intracrine actions due to conversion to androgens and estrogens. The transdermal administration of steroid hormone precursors pregnenolone, DHEA, as well as the natural hormone progesterone, has some important advantages. In recent years, a vast number of products that contain these active ingredients have been sold. An excellent composition for transporting DHEA and progesterone through the skin is an oil-in-water emulsion that contains components of the fatty tissue of the skin along with suitable permeation enhancers and use of liposomes and nanospheres.

Secretion of certain neurotransmitters, such as acetylcholine, is essential for the facial muscle contraction, and inhibition of these neurotransmitters is the basis of most of today's cosmetic formulas directed against expression wrinkles. The secretion and trafficking of proteins between compartments in eukaryotic cells is mediated by carrier vesicles that bud from one organelle and fuse with another one. This transport is mediated in part by SNARE proteins, which comprise conserved families of membrane-associated proteins such as VAMP, syntaxin and SNAP-25 families which mediate membrane fusion.

For example, in the synaptic transmission in response to $Ca^{2+}$ influx, synaptic vesicles containing neurotransmitters fuse with the presynaptic membrane and release their contents into the synaptic cleft. Similarly, at the neuromuscular junction, $Ca^{2+}$ stimulates the exocytosis of presynaptic vesicles containing acetylcholine, which is released into the synaptic cleft. SNARE proteins such as VAMP, syntaxin and SNAP25 are involved in the exocytosis of these vesicles, which contain different neurotransmitters, such as catecholamines (norepinephrine/noradrenaline, epinephrine, and dopamine), acetylcholine, serotonin and/or peptide neurotransmitters, such as enkephalins.

Acetylcholine is one very important neurotransmitter. Release of acetylcholine is important for muscle contraction. Acetylcholine may also be involved in nocioception and chemosensitivity. The inhibition of acetylcholine release may be one method for preventing those muscle contractions that lead to increased facial expression wrinkles.

Most of today's cosmetic formulas directed against facial expression wrinkles are based on the inhibition of acetylcholine secretion which is essential for facial muscle contraction. Botulinum toxin is among the most commonly used molecules against expression wrinkles, mainly for the wrinkles between the eyebrows, at the periphery of the eyes and on the forehead. Even though most botulinum toxins were found to be safe for use in humans, administration of these agents by intra-muscular injections remains an inconvenient method of administration, is immunogenic and can have some adverse effects.

The most frequently reported adverse events in clinical trials for botulinum toxin A (BOTOX®) were dysphagia (19%), upper respiratory infection (12%), neck pain (11%), and headache (11%). Caution should be exercised when administering BOTOX® to individuals with periphery motor neuropathic disease (e.g., amyotrophic lateral sclerosis, motor neuropathy) or neuromuscular junctional disorders (e.g., myasthenia gravis). Furthermore, it cannot be excluded that such toxins could be stored in the central nervous system for long period of time. In any case, botulinum toxin is highly immunogenic.

More recently, to circumvent the intra-muscular injection of toxins, transdermal botulinum toxin compositions and administrations have been described (U.S. Patent Publication 20050074461; U.S. Patent Publication 20050175636). However, presence of a toxin on the skin could be hazardous, due to possible contact with the mouth, nasopharyngeal region and the digestive tract.

While numerous studies have addressed the mode of action of botulinum toxin, many of the aspects have still to be uncovered. BOTOX®, for example, comprises three distinct biological regions, one mediating cell-specific binding, a second mediating cell entry, and a third having protease activity towards various substrates (e.g., SNARE complex proteins VAMP, syntaxin and SNAP-25) (Montecucco et al., *Trends Biochem.* 18:324-327, 1993). Botulinum toxins specifically cleave proteins present in the SNARE complex. These SNARE proteins are involved in the exocytosis of vesicles containing acetylcholine. In the presence of BOTOX®, the last nine amino acids of SNAP25 are removed. This truncated form of SNAP25 is extremely stable and competes with wild type SNAP25. Similarly, VAMP or syntaxin can be cleaved by other classes of botulinum toxins.

An attractive alternative to Botox comprises the production of truncated forms of SNAP25, VAMP and syntaxin which exhibit activities similar to those of botulinum toxin, or to peptides designed to specifically block the release of acetylcholine by acting on the vesicles involved in the exocytosis (the SNARE complex). A peptide (Acetyl hexapeptide-3) (Ac-Glu-Glu-Met-Gln-Arg-Arg-NH2) (SEQ ID NO: 24) that mimics the C-terminal sequence of SNAP-25 has been shown to inhibit secretory vesicle docking in chromaffin cells (Gutierrez et al., *J. Biol. Chem.* 272:2634-2639, 1997). This peptide also affects the release of neurotransmitters by blocking exocytosis. This acetyl hexapeptide (also named ARGIRELINE®, Lipotec SA, Barcelona, Spain) is an anti-wrinkle peptide, which acts through a unique mechanism that relaxes facial tension and leads to a reduction in superficial facial lines and wrinkles. A study published in the International Journal of Cosmetic Science used a 10% concentration of the peptide in an oil/water emulsion. The results showed reduced wrinkle depth up to 30% after a 30-day treatment (V. Kanga, Skin care delivery systems, Happi, 47 (January 2004); International Journal of Cosmetic Science 24:303, 2002). Thus far, the SNAP25 molecule was the target for blocking neurotransmitter release either for BOTOX® or for ARGIRELINE®. The former agent is used in injection, the latter is used as topical.

Based on peptide sequences, the palmitoylated pentapeptide (Pal-KKTTS) (SEQ ID NO: 25) could have a beneficial effect on the skin. Palmitoyl oligo-peptide is a lipophilic modified peptide developed by Sederma SA and owned by Croda and is marketed as MATRIXYL®. Pentapeptides are composed of the amino acids lysine, threonine and serine, which are made lipophilic by the attachment of palmitic acid. This leads to the sequence Pal-Lys-Thr-Thr-Lys-Ser or Pal-KTTKS (SEQ ID NO: 26), a combination that mimics nature's tissue-regenerating processes by signaling the cells of the dermis to synthesize proteins (collagen I, III, IV) and polysaccharides (glycoaminoglycanes, hyaluronic acid) which make up the connective tissue necessary for padding the skin (U.S. Pat. No. 6,620,419). Two teams of investigators say palmitoyl pentapeptide is as effective as retinol in improving the effects of photo-aging but without the side effects often associated with retinol. These were two separate trials supported by Sederma SA. The first study examined the effects of palmitoyl pentapeptide (3 ppm) versus retinol (700 ppm) to the crow's feet area on photo-aged skin. The second study examined the effects of palmitoyl pentapeptide (5 ppm) on the structure of elastin and collagen IV in women with photo-aged skin. Palmitoyl pentapeptide triggered growth in elastin and collagen IV and enhanced the structure of elastin and collagen IV. The peptide was not associated with any side effects and was a safe and potent alternative to retinoids in wrinkle repair.

Oligopeptides obtained by the biotransformation of native proteins from the seeds of Hibiscus esculents L. (okra) is a patented complex in Myoxinol LS 9736 (Cognis, Cincinnati, Ohio). It is primarily composed of low molecular weight oligopeptides, allowing good bioavailability. These botanical peptides combat wrinkles in a similar way to botulinum toxin, by inhibiting the mechanical factors responsible for the appearance of expression lines on the face. This novel active ingredient has a dual action, working biologically to retard the aging of cells (anti-free radical activity), and mechanically to inhibit facial muscle contraction. Botulinum toxin prevents the formation of dynamic wrinkles such as horizontal and vertical frown lines across the forehead, crow's feet around the eyes and naso-labial lines around the mouth. The ingredient's potential as an anti-wrinkle agent was measured using an in vitro test on contraction of innervated muscle cells. The ingredient's ability to inhibit the spontaneous contraction of muscle cells was evaluated by recording the frequency of contractions over 24 hours using Carisoprodol, a known muscle relaxant, as a positive control. Cognis reported that a cream containing 1% Myoxinol LS 9736 applied to the crow's feet area over a three-week period suggested considerable anti-aging properties. The cream resulted in smoother skin, and wrinkles were 26% less noticeable due to significant reduction in muscle cell contractions, the primary mechanical factor responsible for the appearance of dynamic facial wrinkles. The contraction-inhibiting effect stops 24 hours after application.

Other synthetic peptides that mimic the amino acid sequence of segments from SNARE proteins have been used to investigate the functional role of proteins implicated in the secretory pathway, such as ESUP-A (Gutierrez et al., *J. Biol. Chem.* 272:2634-2639, 1997). Often the use of the synthetic peptide is limited by the difficulty in entering the target cell and an artificial system requiring permeabilization of the cell by saponin is necessary to mediate an effect of the synthetic peptide. This problem could be circumvented by fusing synthetic peptides to a domain known to translocate peptide or protein into cells such as known protein translocation domains (PTD). PTDs, such as a segment of TAT protein of HIV have been extensively studied and are known as efficient approach to transduce proteins into different cell type (for a review see Dietz et al., *Mol. Cell. Neurosci.* 27: 85-131, 2004). The basic transduction domain of HIV has also been shown to mediate translocation into various organs of mice. Intraperitoneal or intravenous injection of the PTD fusion protein resulted in delivery of the protein in various organs, including brain. On the contrary, there is only one example of the topical penetration of a catalase protein when fused to TAT PTD or to 9-Arginine (9R) (Jin et al., *Free Radical Biology and Medicine,* 31:1509-1519, 2001). However, no effect on the release of neurotransmitter was shown when the TAT PTD or 9-Arginine (9R) was used alone. Similarly, 9-polylysine enhanced penetration of superoxide dismutase into mammalian skin (Park et al., *Molecules and Cells* 13:202-208, 2002).

Aside from the SNAP 25 sequence, no other peptides have been reported to block neurotransmitter release. U.S. Pat. No. 6,794,362 describes use of peptides derived from the elastin protein for use in cosmetic compositions. U.S. Pat. No. 6,358,929 describes use of Lysine-Proline-Valine (KPV) peptides and derivatives as additives in a cosmetic composition intended to suppress or reduce contact hypersensitivity reactions. U.S. Pat. No. 6,183,759 describes synthesis of peptides conjugated to lanolin-derived non-hydroxyl fatty acids for use in cosmetic compositions.

Additionally, the binding of acetylcholine to its receptor on the muscle cell triggers muscle contraction. The contraction of a muscle involves transient interaction of myosin and actin. Myosin is organized in thick filaments whereas actin is polymerized in thin filaments (F-actin). Muscle contraction occurs by the sliding of the thin and the thick filaments past each other. The assembly also includes minor muscle proteins a-actinin, desmin, vimentin and nebulin. Alteration in the filaments formation, such as alteration of the actin polymerization could be one way to avoid muscle contraction and provoke muscle relaxation.

In injured muscles, wound healing is often retarded by a fibrotic process. Specific growth factors such as TGF-β are involved in this fibrotic process. Overexpression of TGF-β leads to events which cause increased deposit of matrix proteins leading to fibrosis. Activation/processing of TGF-β by specific enzymes such as the proconvertases (e.g. furin among others) is a key event in the fibrotic process. Blocking the activation of TGF-β via proconvertases could be beneficial in wound healing.

Thus, there remains a need in the art to identify peptide sequences that have pleiotropic functions such as inhibiting neurotransmitter release and inhibiting muscle contraction, and simultaneously provoking muscle relaxation, and are useful as a treatment for wrinkles and for injured muscles.

SUMMARY OF THE INVENTION

The present invention relates to identification of peptides that act as inhibitors of neurotransmitter release and use of these peptides to block neurotransmitter release in biological functions, such as muscle contraction and to induce muscle relaxation. Further disclosed is the use of these peptides in a composition suitable for application to the skin to inhibit neurotransmitter secretion, to prevent muscle contraction and to treat wrinkles and fine lines. Further disclosed is the use of these peptides on muscle cells to induce muscle cell relaxation.

In one embodiment, the invention provides a composition comprising one or more peptides selected from the group consisting of SEQ ID NOs: 1-23. In one aspect the composition comprises 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, up to 22 or more peptides selected from the group consisting of SEQ ID NOs: 1-23. In another aspect, the invention provides compositions comprising one or more peptides having at least 80% identify to the peptides set out in SEQ ID NOs: 1-23. It is contemplated that the peptides share at least 80%, 85% 90%, 95%, 96%, 97%, 98%, or 99% identity with any one of the peptides set out in SEQ ID NO: 1-23. In a related embodiment the compositions comprise one or more of SEQ ID NO: 24-29.

In a further aspect, the present invention provides a peptide composition as set out above wherein the peptides comprise L-enantiomers of the desired amino acids or D-enantiomers of the amino acids, or a mixture of L- or D-enantiomers of the desired amino acids. In a related aspect, the invention contemplates that the peptide compositions may be, or may further comprise, one or more retro-inverso isomers of one or more of the peptides set out in SEQ ID NOs: 1-23.

In another embodiment, it is contemplated that the compositions of the invention comprise one or more peptides wherein one or more peptides is a fusion protein. In one aspect, the peptides of the invention are fused to all or part of a second protein. In a related aspect, one or more peptides in a composition is/are fused to a translocation domain. In another aspect the protein translocation domain is derived from the HIV TAT protein. In a further aspect, the protein translocation domain is an arginine-rich sequence. In a still further aspect, the peptide is fused to the lipolytic peptide GKH. Other protein translocation domains contemplated by the invention include, but are not limited to, pentratin-1, the antennapedia translocation domain, L-arginine oligomers, D-arginine oligomers, L-lysine oligomers, D-lysine oligomers, L-histidine oligomers, D-histidine oligomers, L-ornithine oligomers, D-ornithine oligomers, HSV-1 protein VP22 and fragments thereof, peptides having at least six contiguous amino acid residues that are L-arginine, D-arginine, L-lysine, D-lysine, L-histidine, D-histidine, L-ornithine, D-ornithine, or a combination thereof; and peptide analogs thereof.

In a related aspect, the peptides of the invention are fused to a nucleic acid, including but not limited to DNA, RNA (single or double stranded) or RNAi.

In one variation, the peptides of the invention are further modified for purposes related to increased shelf-life; increased stability; increased circulating in-vivo half-life of the peptide in a mammal; reduced systemic toxicity, and the like. Standard pharmaceutical and formulation chemistry is used to achieve such goals, e.g., through glycosylation, pegylation, introduction of non-hydrolyzable bonds, mixing with pharmaceutically acceptable diluents, adjuvants, or carriers, and the like.

In one aspect the peptide compositions comprise at least one active agent selected from the group consisting of moisturizers, de- and pro-pigmenting agents, desquamating agents, UV absorbing agents, sunscreen active agents, viscosity modifying agents, abrasive agents, pH adjustors, anti-glycation agents, anti-oxidative agents, NO-synthase inhibitors agents, agents stimulating the synthesis of dermal and/or epidermal macromolecules, agents preventing the degradation of dermal and/or epidermal macromolecules, agents stimulating the synthesis of collagen, agents preventing the degradation of collagen, agents stimulating fibroblasts and/or keratinocyte proliferation or for stimulating keratinocyte differentiation, muscle relaxants, dermo relaxants, rejuvenating agents, anti-pollution agents and free-radical scavengers, agents acting on capillary circulation, agents acting on the metabolism of cells, anti-inflammatory agents, anti-perspiring agents, anti-microbial and anti-fungal agents, with adjuvant hydrophilic and lipophilic gel, active, preserving, solvents, fragrances, fillers, pigments, odor absorbers.

In another embodiment, it is contemplated that the concentration of the one or more peptides in the peptide composition is from 0.00001% to 10% (w/w) of the total weight of the composition. In one aspect, the concentration of the one or more peptides peptide is about 0.001 to 1% (w/w). In a related embodiment, the invention provides a unit dose of the peptide, preferably contained in a container labeled with the contents of the container and instructions for administration to a subject.

In one embodiment, the composition of the invention is an oil-in-water emulsion. In a related embodiment, the composition is a water-in-oil immersion. In a further embodiment, the peptide composition of the invention is formulated for topical use.

Peptides of the invention can be made using synthetic techniques and recombinant DNA techniques. As such, the invention further provides purified and isolated polynucleotides comprising nucleotide sequences that encode peptides of the invention; vectors (especially expression vectors) comprising such polynucleotides; host cells comprising the polynucleotides or the vectors; and methods of making the peptides using the polynucleotides, vectors, or host cells. For example, provided is a method for transforming a host cell comprising the step of introducing a vector according comprising a polynucleotide into said host cell, expressing the polynucleotide said host cell and purifying the resultant peptide. Also provided is a host cell transformed by the method above. If the peptide is expressed as a fusion with a partner, it may be desirable to cleave the fusion to obtain purified peptide.

It will be apparent from the description herein that the invention provides a number of methods and applications involving the compositions of the invention. In one embodiment, the invention provides a method of inhibiting neurotransmitter secretion of a cell comprising contacting a cell that secretes neurotransmitters with a composition of the invention in an amount effective to inhibit neurotransmitter secretion by the cell. Contemplated target cells known to express neurotransmitters include, but are not limited to, adult brain and neuronal cells, muscle cells, epithelial cells and neuroepithelial cells, retina, neuroendocrine cells and Merkel cells in the skin. In one preferred variation, the contacting step comprises contacting the cell with a composition comprising the peptide in a pharmaceutically acceptable carrier.

In a related embodiment, the invention provides a method of inhibiting muscle contraction in a mammalian subject comprising administering to a mammalian subject a composition comprising one or more peptides of the invention, in an amount effective to inhibit muscle contraction.

In a related embodiment, the invention provides a method of inducing muscle relaxation in a mammalian subject comprising administering to a mammalian subject a composition comprising one or more peptides of the invention, in an amount effective to induce muscle relaxation.

In a further embodiment, the invention provides a method for treating facial expression wrinkles comprising administering to a mammalian subject exhibiting facial expression wrinkles a composition comprising one or more peptides of the invention, in an amount effect to reduce depth of wrinkle creases or increase in wrinkle size. It is contemplated that a facial expression wrinkle as used herein refers to such wrinkles resulting from repeated facial expressions including wrinkles commonly referred to as crow's feet, periorbital wrinkles, laugh lines, brow furrow, wrinkles around the lips, downturned mouth corners, glabellar rhytides (vertical frown lines), and wrinkles in the neck. It will be appreciated that any reduction in the rate of wrinkle size is indicative of successful treatment. In one aspect, wrinkle depth is improved by about 10-100%. In a related aspect, wrinkle depth is improved by about 10%, about 20%, about 30%, about 40%, about 50%, about 60%, about 70%, about 80% or about 90%. In a further aspect, wrinkles shrink or are eradicated entirely.

In one variation, the invention provides a method for enhancing wound healing comprising the step of administering to a subject in need of wound healing an effective amount of a composition comprising one or more peptides of the invention. In another variation, the invention provides a method for enhancing wound healing by blocking the fibrotic process comprising the step of administering to a subject in need of wound healing an effective amount of a composition comprising one or more peptides of the invention.

In a further variation, the invention provides methods for treating other disorders related to neurotransmitter release and muscle contraction selected from the group consisting of hyperhydrosis, focal dystonia, nondystonic disorders, inflammation, and pain, comprising the step of administering to a subject in need an effective amount of a composition comprising one or more peptides of the invention.

Enhancement of the therapeutic utility of the peptides of the invention is possible by delivery of additional therapeutic agents with the peptides. In one variation, peptides can be co-administered with other therapeutic agents. Such therapeutic agents include, but are not limited to, neurotransmitter inhibitors, anti-pain medications, vasoconstrictors, apoptosis inhibitors, anti-inflammatory agents.

In one aspect, the invention provides peptide compositions of the invention further comprising one or more neurotransmitter inhibitors and muscle relaxants selected from the group consisting of curare, α-bungarotoxin, conotoxin, alcuronium, gallamine, pancuronium, atracurium, vecuronium, Pirenzepine AF-DX 116 pF-HHSiD, ipratroprium, scopolamine and atropine Neurotransmitters that may be inhibited by the peptide compositions of the invention include Acetylcholine (ACh), Dopamine (DA), Norepinephrine (NE), Serotonin (5-HT), Histamine, Epinephrine, Gamma-aminobutyric acid (GABA), Glycine, Glutamate, Aspartate, bradykinin, beta-endorphin, bombesin, calcitonin, cholecystokinin, enkephalin, dynorphin, insulin, gastrin, substance P, neurotensin, glucagons, secretin, somatostatin, motilin, vasopressin, oxytocin, prolactin, thyrotropin, angiotensin II, sleep peptides, galanin, neuropeptide Y, thyrotropin-releasing hormone, gonadotropin-releasing hormone, growth hormone-releasing hormone, luteinizing hormone, and vasoactive intestinal peptide.

It is contemplated that the foregoing methods can be performed in vitro or can be performed in vivo, by administering the peptide to an organism that comprises the target cell. In one aspect, contacting is performed by a route selected from the group consisting of subcutaneous, transdermal, topical, intradermal, and subdermal.

In still another variation, the invention contemplates a method for improving the appearance of the skin, the method comprising applying topically a cosmetic comprising a composition of the invention and a cosmetically acceptable vehicle. In one aspect, said skin is aged, photoaged, dry, lined or wrinkled. Cosmetically acceptable vehicles may include, but are not limited to water, liquid or solid emollients, solvents, humectants, thickeners and powders, which are described in further detail herein.

It is further contemplated that the cosmetic composition further comprises one or more of estradiol; progesterone; pregnanalone; coenzyme Q10; methylsolanomethane (MSM); copper peptide (copper extract); plankton extract (phytosome); glycolic acid; kojic acid; ascorbyl palmitate; all trans retinol; azaleic acid; salicylic acid; broparoestrol; estrone; adrostenedione; and androstanediols. In a related aspect the composition further comprises a sunblock. In one variation, said cosmetically acceptable vehicle is an oil in water, or water in oil, emulsion. In a second variation, said composition is selected from the group consisting of an emulsion, lotion, spray, aerosol, powder, ointment, cream and foam.

BRIEF DESCRIPTION OF THE DRAWINGS

FIG. 1 presents a table setting forth peptide sequences contemplated by the invention.

FIG. 6 shows the effects of various furin inhibitors (FIG. 6A, ion chelators; FIG. 6B, furin inhibitor RVKR.

FIG. 7 shows the staining of PC12-ES cells after treatment with L-Bel1. FIG. 7A shows staining of L-Bel-1 alone while

DETAILED DESCRIPTION

Figure 2:
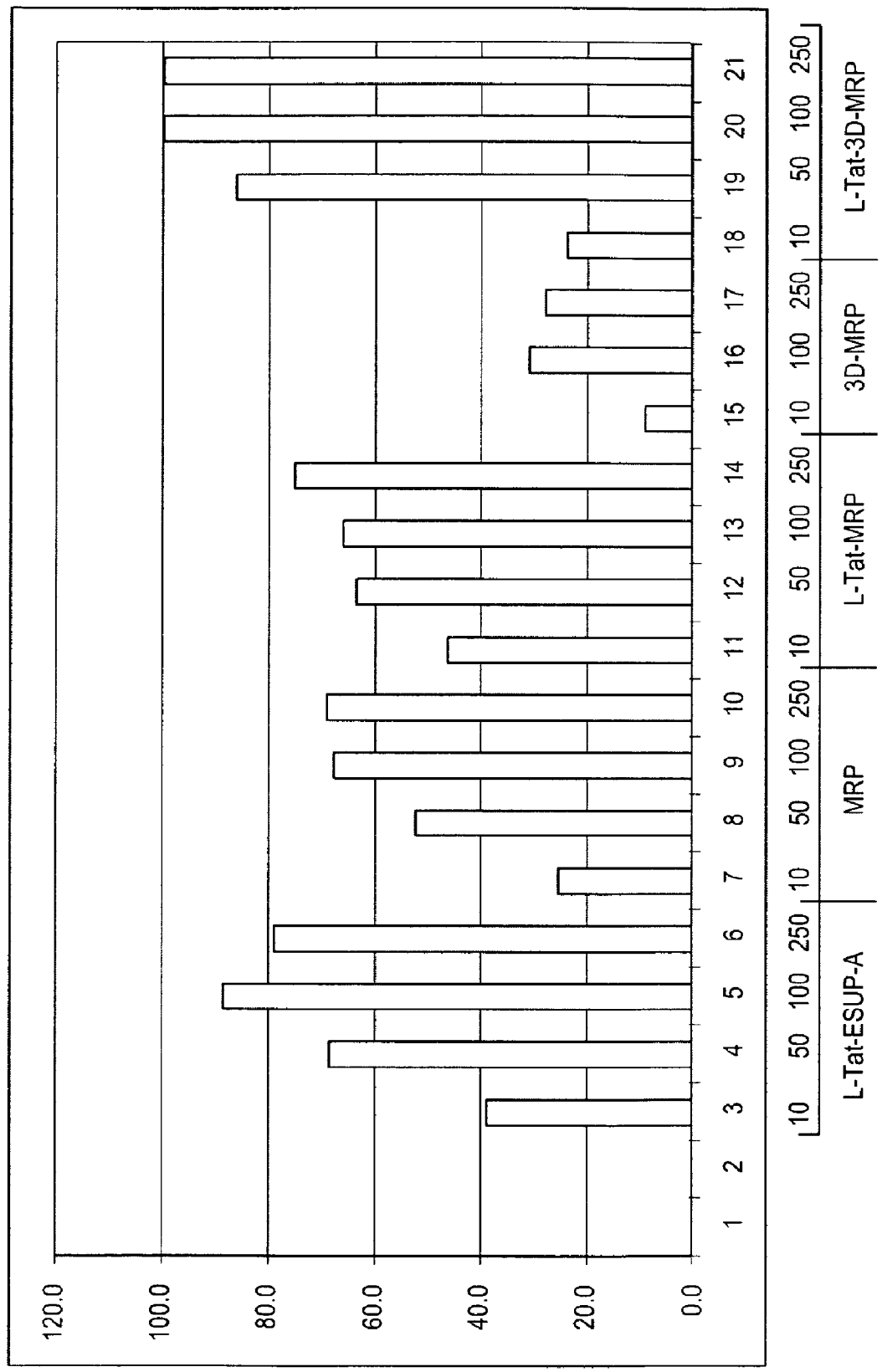
FIG. 2 shows dose dependent inhibition of neurosecretion of PC12 cells by peptides MRP, L-Tat-MRP, 3D-MRP, and L-Tat-3D-MRP.

The present invention relates to identification of therapeutically beneficial peptides and use of these peptides.

Peptides of the Invention. It is contemplated that the peptides of the invention, such as those exemplified in FIG. 1 are active as L amino acid peptides or as D amino acid peptides. L amino acids are those amino acids typically found in naturally synthesized peptides. L amino acids are the amino acids expressed in the L conformation.

D amino acids are the enantiomeric form of L amino acids and are not typically incorporated into naturally synthesized peptides. It is contemplated that the peptides of the invention are active as D-enantiomeric amino acid peptides, i.e., the same sequence from $NH_2$ to COOH ends, but each amino acid is a D-enantiomer.

In one embodiment, the peptides of the present invention are non-hydrolyzable. To provide such peptides, one may select peptides from a library of non-hydrolyzable peptides, such as peptides containing one or more D-amino acids or peptides containing one or more non-hydrolyzable peptide bonds linking amino acids. Also contemplated by the invention are all-D-retro-inverso peptides.

The term "retro-inverso peptide" refers to an isomer of a linear peptide in which the direction of the sequence is reversed, and the term "D-retro-inverso isomer" refers to an isomer of a linear peptide in which the direction of the sequence is reversed and the chirality of each amino acid residue is inverted. See, e.g., Jameson et al., *Nature* 368:744-46, 1994; Brady et al., *Nature* 368:692-93, 1994, Guichard et al., *J. Med. Chem.* 39:2030-39, 1996. The retro-peptides are produced by classical F-mock synthesis and further analyzed by Mass Spectrometry. They are purified by HPLC using techniques known in the art.

An all-D retro-inverso peptide of the invention would provide a peptide with functional properties similar to the native peptide, wherein the side groups of the component amino acids would correspond to the native peptide alignment, but would retain a protease resistant backbone. To illustrate, if the naturally occurring TAT protein (formed of L-amino acids) has the sequence RKKRRQRRR (amino acids 4-12 of SEQ ID NO: 3), the retro-inverso peptide analog of this peptide (formed of D-amino acids) would have the sequence RRRQRRKKR (reverse of amino acids 4-12 of SEQ ID NO: 3). D-amino acid peptides (direct sequence or retroinverso) could be applied to other peptides such as Argireline (acetylhexapeptide) or Pal-KTTKS (SEQ ID NO: 26).

The net result of combining D-enantiomers and reverse synthesis is that the positions of carbonyl and amino groups in each amide bond are exchanged, while the position of the side-chain groups extending from the alpha carbon is preserved. Unless specifically stated otherwise, it is presumed that any given L-amino acid sequence of the invention may be made into an D retro-inverso peptide by synthesizing a reverse of the sequence for the corresponding native L-amino acid sequence.

In one embodiment, it is contemplated that a peptide of the invention is cross-linked to a side chain of any one of the peptides described herein. This method is used to crosslink similar peptides or the peptides of the invention to each other to generate branched peptides. In one aspect, branching may be at the N- or C-terminus. Crosslinking may also be carried out on internal amino acids resulting in internal branching, or carried out at the N- or C-terminus and internal positions simultaneously.

The peptides of the invention can be active as modified peptides. Modifications contemplated by the invention include, but are not limited to, pegylation (PEG linkage), glycosylation, amidation, carboxylation, phosphorylation, or addition of an acetyl, myristic, palmitic, stearic, or acidic group, creation of acid addition salts, amides, esters, in particular C-terminal esters, and N-acyl derivatives of the peptides of the invention. The peptides also can be modified to create peptide derivatives by forming covalent or noncovalent complexes with other moieties. Covalently-bound complexes can be prepared by linking the chemical moieties to functional groups on the side chains of amino acids comprising the peptides, or at the N- or C-terminus.

Peptides of the invention can be either linear or cyclic, and are produced by natural or synthetic means. For example, disulfide bonds between cysteine residues may cyclize a peptide sequence. Bifunctional reagents can be used to provide a linkage between two or more amino acids of a peptide. Other methods for cyclization of peptides, such as those described by Anwer et al. (*Int. J. Pep. Protein Res.* 36:392-399, 1990) and Rivera-Baeza et al. (*Neuropeptides* 30:327-333, 1996) are also known in the art.

In particular, it is contemplated that the peptides of the invention can be conjugated to a reporter group, including, but not limited to a radiolabel, a fluorescent label, an enzyme (e.g., that catalyzes a calorimetric or fluorometric reaction), a substrate, a solid matrix, or a carrier (e.g., biotin or avidin) Such labels are well known to those of skill in the art. Labels are described in, for example, U.S. Pat. No. 3,817,837; U.S. Pat. No. 3,850,752; U.S. Pat. No. 3,996,345, U.S. Pat. No. 4,277,437; U.S. Pat. No. 3,817,837; U.S. Pat. No. 3,850,752; and U.S. Pat. No. 3,939,350. Any of the peptides of the present invention may comprise one, two, or more of any of these labels.

It is further contemplated that the peptides of the invention can be conjugated to inhibitory groups (e.g., fluoromethylketone or chloromethylketone) to block the activity of an enzyme. The peptides of the invention can also act as competitors of natural substrates.

Analogs or variants of the peptides of the invention are also contemplated. Variants and analogs may be substantially homologous or substantially identical to the peptides described herein. Preferred variants and analogs are those which have the same characteristics of the peptides of the invention, such as inhibition of neurosecretion or inhibition of muscle contraction. Peptide analogs or variants are those peptide variants having a minimum percent amino acid identity to the amino acid sequence of a peptide set out in SEQ ID NOs: 1-23 (e.g., at least 80, 85, 90, 91, 92, 93, 94, 95, 96, 97, 98, or 99% identity preferred).

Substitutional variants typically exchange one amino acid of the peptide sequence for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge, as described below.

The term "conservative substitution" as used herein denotes the replacement of an amino acid residue by another, biologically similar residue with respect to hydrophobicity, hydrophilicity, cationic charge, anionic charge, shape, polarity and the like. As such, it should be understood that in the context of the present invention, a conservative substitution is recognized in the art as a substitution of one amino acid for another amino acid that has similar properties. Examples of conservative substitutions include the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic acid for aspartic acid, or glutamine for asparagine, and the like. Neutral hydrophilic amino acids which can be substituted for one another include asparagine, glutamine, serine and threonine. The term "conservative substitution" also includes the use of a substituted or modified amino acid in place of an unsubstituted parent amino acid provided that antibodies raised to the substituted polypeptide also immunoreact with the unsubstituted polypeptide. By "substituted" or "modified" the present invention includes those amino acids that have been altered or modified from naturally occurring amino acids.

The invention also contemplates use of the peptides as propeptides, which are cleaved inside the host cell to generate an active form of the peptide of interest. Recombinant synthesis of propeptides is described in, for example, Wu et al. (*Proc Natl Acad Sci USA*. 94:13654-60, 1997).

In one embodiment, the peptides of the invention are fused at the $NH_2$— or COOH terminus of different peptides to generate fusion proteins. The peptides may be fused to proteins such as targeting proteins, receptor-specific ligands, enzymes, antibodies, translocation domains, or other proteins or protein domains which may target the peptide to a specific tissue or cell type to enhance the utility of the peptides of the invention.

It is contemplated that the peptides of the invention are active as fusion peptides fused to other active peptides such as: Argireline acetyl AGGEEMQRR (SEQ ID NO: 27); F6L9Y10F14 (SMEAFAKLYAEAFAKG) (SEQ ID NO: 28); Pal-KTTKS (SEQ ID NO: 26); ESUP-A (NH2-SNKTRIDE-ANQRATKMLGSG-COOH (SEQ ID NO: 29); Botulinum toxin A or another botulinum toxin B, C, D, E, F and G (Montecucco et al., *Curr Opin Pharmacol*. 5:274-9, 2005).

In a related embodiment, the peptides of the invention are fused to nucleic acids such as DNA, RNA single or double stranded or RNAi.

Translocation domains are found in many different proteins in addition to the HIV Tat protein. Other sources for translocating peptides are well known in the art. For example, HSV-1 protein VP22 (described in, e.g., WO 97/05265; Elliott and O'Hare, *Cell* 88: 223-233, 1997)), or non-viral proteins (Jackson et al, *Proc. Nat. Acad. Sci. USA* 89: 10691-10695, 1992) exhibit translocating properties. Other suitable translocating or trafficking peptides include peptides derived from the *Drosophila melanogaster* antennapedia (Antp) homeotic transcription factor, the h region of the signal sequence of Kaposi fibroblast growth factor (MTS), and the protein PreS2 of hepatitis B virus (HBV) (Kelemen, et al., *J. Biol. Chem*. 277:8741-8748, 2002).

Alternatively, the translocating peptide is a polymer of cationic macromolecules or an arginine-rich peptide including a poly-arginine repeat. In a still further aspect, the peptide is fused to the lipolytic peptide GKH which also translocates proteins across membranes. Other protein translocation domains contemplated by the invention include, but are not limited to, pentratin-1, the antennapedia translocation domain, L-arginine oligomers, D-arginine oligomers, L-lysine oligomers, D-lysine oligomers, L-histidine oligomers, D-histidine oligomers, L-ornithine oligomers, D-ornithine oligomers, peptides having at least six contiguous amino acid residues that are L-arginine, D-arginine, L-lysine, D-lysine, L-histidine, D-histidine, L-ornithine, D-ornithine, homoarginine, N-methyl-lysine, N,N-dimethyl-Lys, N,N,N-trimethyl lysine, any unnatural basic amino acid (such as N-1-(2-pyrozolinyl)-Arginine or any unnatural amino acid carrying a guanidino group, or combinations thereof; and peptide analogs thereof.

A peptide for use in the invention and a translocating or trafficking sequence can be linked by chemical coupling in any suitable manner known in the art. Many known chemical cross-linking methods are non-specific, i.e.; they do not direct the point of coupling to any particular site on the transport polypeptide. As a result, use of non-specific cross-linking agents may attack functional sites or sterically block active sites, rendering the conjugated proteins biologically inactive.

One way to increase coupling specificity is by direct chemical coupling to a functional group found only once or a few times in one or both of the polypeptides to be cross-linked. For example, in many proteins, cysteine, which is the only protein amino acid containing a thiol group, occurs only a few times. Also, for example, if a polypeptide contains no lysine residues, a cross-linking reagent specific for primary amines will be selective for the amino terminus of that polypeptide. Successful utilization of this approach to increase coupling specificity requires that the polypeptide have the suitably rare and reactive residues in areas of the molecule that may be altered without loss of the molecule's biological activity.

Methods of Making Peptides. The peptides of the present invention can be synthesized in solution or on a solid support in accordance with conventional techniques. Various automatic synthesizers are commercially available and can be used in accordance with known protocols. See, for example, Stewart and Young, *Solid Phase Peptide Synthesis*, 2d. ed., Pierce Chemical Co., (1984); Tam et al., *J. Am. Chem. Soc*. 105:6442, 1983; Merrifield, *Science* 232:341-347, 1986; and Barany and Merrifield, The Peptides, Gross and Meienhofer, eds, Academic Press, New York, 1 284; Barany et al., *Int. J. Peptide Protein Res*. 30:705-739, 1987; and U.S. Pat. No. 5,424,398, each incorporated herein by reference.

Solid phase peptide synthesis methods use a copoly(styrene-divinylbenzene) containing 0.1-1.0 mMol amines/g polymer. These methods for peptide synthesis use butyloxy-carbonyl (t-BOC) or 9-fluorenylmethyloxy-carbonyl (FMOC) protection of alpha-amino groups. Both methods involve stepwise syntheses whereby a single amino acid is added at each step starting from the C-terminus of the peptide (See, Coligan, et al., Current Protocols in Immunology, Wiley Interscience, 1991, Unit 9). On completion of chemical synthesis, the peptides can be deprotected to remove the t-BOC or FMOC amino acid blocking groups and cleaved from the polymer by treatment with acid at reduced temperature (e.g., liquid HF-10% anisole for about 0.25 to about 1 hours at 0° C.). After evaporation of the reagents, the peptides are extracted from the polymer with 1% acetic acid solution which is then lyophilized to yield the crude material. The crude material can normally be purified by such techniques as gel filtration on Sephadex G-15 using 5% acetic acid as a solvent. Lyophilization of appropriate fractions of the column will yield the homogeneous peptide or peptide derivative, which can then be characterized by such standard techniques as amino acid analysis, thin layer chromatography, high performance liquid chromatography, ultraviolet absorption spectroscopy, molar rotation, solubility, and quantitated by the solid phase Edman degradation.

Alternatively, a variety of expression vector/host systems may be utilized to contain and express the peptides of the invention. These include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems.

Mammalian host systems for the expression of the recombinant protein also are well known to those of skill in the art. Host cell strains may be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Different host cells such as CHO, HeLa, MDCK, 293, W138, and the like have specific cellular machinery and characteristic mechanisms for such post translational activities and may be chosen to ensure the correct modification and processing of the introduced, foreign protein. Mammalian cells that are useful in recombinant protein productions include, but are not limited to, VERO cells, HeLa cells, Chinese hamster ovary (CHO) cell lines, COS cells (such as COS 7), W138, BHK, HepG2, 3T3, RIN, MDCK, A549, PC12, K562 and 293 cells. Exemplary protocols for the recombinant expression of the protein are described herein below.

The peptides of the invention may also be recombinantly expressed in yeast using a commercially available expression system, e.g., the *Pichia* Expression System (Invitrogen, San Diego, Calif.), following the manufacturer's instructions. This system also relies on the pre-pro-alpha sequence to direct secretion, but transcription of the insert is driven by the alcohol oxidase (AOX1) promoter upon induction by methanol.

The secreted peptide is purified from the yeast growth medium by, e.g., the methods used to purify the peptide from bacterial and mammalian cell supernatants.

Alternatively, the peptide may be expressed in an insect system. Insect systems for protein expression are well known to those of skill in the art. In one such system, *Autographa californica* nuclear polyhedrosis virus (AcNPV) is used as a vector to express foreign genes in *Spodoptera frugiperda* cells or in *Trichoplusia larvae*. The peptide coding sequence is cloned into a nonessential region of the virus, such as the polyhedrin gene, and placed under control of the polyhedrin promoter. Successful insertion of the peptide will render the polyhedrin gene inactive and produce recombinant virus lacking coat protein coat. The recombinant viruses are then used to infect *S. frugiperda* cells or *Trichoplusia larvae* in which peptide is expressed (Engelhard et al., *Proc Nat Acad Sci* 91: 3224-7, 1994).

In another example, the DNA sequence encoding the peptide is amplified by PCR and cloned into an appropriate vector for example, pGEX-3X (Pharmacia, Piscataway, N.J.). The pGEX vector is designed to produce a fusion protein comprising glutathione-S-transferase (GST), encoded by the vector, and a protein encoded by a DNA fragment inserted into the vector's cloning site. The primers for the PCR may be generated to include for example, an appropriate cleavage site.

Where the fusion partner is used solely to facilitate expression or is otherwise not desirable as an attachment to the peptide of interest, the recombinant fusion protein may then be cleaved from the GST portion of the fusion protein.

Alternatively, the DNA sequence encoding the peptide may be cloned into a plasmid containing a desired promoter and, optionally, a leader sequence (see, e.g., Better et al., *Science,* 240:1041-43, 1988). The sequence of this construct may be confirmed by automated sequencing. The plasmid is then transformed into *E. coli* strain MC1061 using standard procedures employing $CaCl_2$ incubation and heat shock treatment of the bacteria (Sambrook et al., supra). The transformed bacteria are grown in LB medium supplemented with carbenicillin, and production of the expressed protein is induced by growth in a suitable medium. If present, the leader sequence will effect secretion of the peptide of the invention and be cleaved during secretion.

Formulations and Routes for Administration. In order to prepare a composition of the invention for clinical use, it is necessary to prepare the peptides of the present invention as pharmaceutical compositions, i.e., in a form appropriate for in vivo applications. Generally, formulation of compositions for clinical use will entail preparing compositions that are essentially free of pyrogens, as well as other impurities that could be harmful to humans or animals. For preparation of pharmaceutical compositions see Remington's Pharmaceutical Science, 18th ed., Mack Publishing Company, Easton, Pa. (1990).

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the peptide or an expression vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The active compositions of the present invention include classic pharmaceutical preparations. Administration of these compositions according to the present invention will be via any common route so long as the target tissue is available via that route. The pharmaceutical compositions may be introduced into the subject by any conventional method, e.g., by intravenous, intradermal, intramusclar, retrobulbar, oral, transdermal, or topical delivery, or by surgical implantation at a particular site. The treatment may consist of a single dose or a plurality of doses over a period of time.

The active compounds may be prepared for administration as solutions of free base or pharmacologically acceptable salts in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle that contains the basic dispersion medium and the required other ingredients from those enumerated above. In the case of sterile powders for the preparation of sterile injectable solutions, the preferred methods of preparation are vacuum drying and freeze drying techniques that yield a powder of the active ingredient plus any additional desired ingredient from a previously sterile filtered solution thereof.

For oral administration the polypeptides of the present invention may be incorporated with excipients and used in the form of non ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration.

"Unit dose" is defined as a discrete amount of a therapeutic composition dispersed in a suitable carrier. Parenteral administration may be carried out with an initial bolus followed by continuous infusion to maintain therapeutic circulating levels of drug product. Those of ordinary skill in the art will readily optimize effective dosages and administration regimens as determined by good medical practice and the clinical condition of the individual patient.

For topical administration, it is contemplated that a composition comprising one or more peptides of the invention at a concentration from about 5% to about 50% w/v. It is further contemplated that the composition for topical administration may contain about 10%, about 15%, about 20%, about 25%, about 30%, about 35%, about 40% or about 45% peptides of the invention. It is also provided that the composition of the invention may comprise a total concentration of the one or more peptides from about 0.00001% to about 10% (w/w) of the total weight of the composition. The compositions may comprise from about 0.001 to about 5%, from about 0.001 to about 1%, or from 0.01% to about 1% w/w total concentration of the one or more peptides.

The frequency of dosing will depend on the pharmacokinetic parameters of the agents and the routes of administration. The optimal pharmaceutical formulation will be determined by one of skill in the art depending on the route of administration and the desired dosage. See for example Remington's Pharmaceutical Sciences, 18th Ed. (1990, Mack Publ. Co, Easton Pa. 18042) pp 1435-1712, incorporated herein by reference. Such formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein as well as the pharmacokinetic data observed in animals or human clinical trials.

Appropriate dosages may be ascertained through the use of relevant dose-response data. The final dosage regimen will be determined by the attending physician, considering factors that modify the action of drugs, e.g., the drug's specific activity, severity of the damage and the responsiveness of the patient, the age, condition, body weight, sex and diet of the patient, the severity of any infection, time of administration and other clinical factors. As studies are conducted, further information will emerge regarding appropriate dosage levels and duration of treatment for specific diseases and conditions.

These compositions of the invention are contemplated for use in iontophoresis or ElectroMotive Drug Administration (EMDA) which is an effective method of delivering drugs to an affected site via electric current, e.g., into a joint or small body part. It is non-invasive, painless and it eliminates potential side effects and adverse reactions which can occur with medications delivered orally or by injection.

Transdermal administration may be performed using a standard trandermal patch, a patch with microprocessor for periodic release of the composition, a patch with microneedles with ultrasound devices, or electric devices. The peptide compositions can also be used in transdermal administration by disrupting the stratum corneum of the patient's skin (chemically, or non chemically, abrasive removal, adhesive removal, cellophane tape, ultrasound, electric current) with or without an enhancing agent. Tat fused to superoxide dismutase can cross the stratum corneum. The composition may also be delivered using combinations of different transdermal administration such as abrasive and ultrasound.

Cosmetic Preparations. The peptide compositions contemplated by the invention may be formulated as cosmetic preparations for topical use and application for cosmetic purposes. The term "cosmetic," as used herein, refers to a substance or preparation which preserves, restores, or enhances the appearance of tissue or skin. The compounds and compositions of the present invention may also be useful as an agent for modifying tissue, especially skin. The term "modify" is used to mean that the present invention changes either the appearance, form, characteristics and/or the physical attributes of the tissue to which it is being provided, applied or administered. The change in form can be reflected in any of the following alone or in combination: enhanced appearance of the skin; increased softness of the skin; increased turgor of the skin; increased texture of the skin; increased elasticity of the skin; and decreased wrinkle formation in the skin.

Examples of cosmetics include emollient emulsions, milky lotions, nourishing emulsions, cleansing emulsions, and like emulsions; emollient creams, massage creams, cleansing creams, makeup creams, and like creams; and the like. These cosmetics are applied to the skin in a suitable amount per application or with a suitable frequency per day, according to the age of the user, the gender, the intended use, the condition of the affected part of the skin, etc. (U.S. Pat. No. 6,946,436). Additional cosmetic preparations are described in International Cosmetic Ingredient Dictionary and Handbook Vol. 4 (9th ed. 2002). The disclosure of the International Cosmetic Ingredient Dictionary and Handbook Vol. 4, is hereby incorporated by reference.

In one embodiment it is contemplated that the cosmetic preparations comprising the peptide compositions of the invention may optionally comprise other skin benefit materials. These include, but are not limited to estradiol; progesterone; pregnanalone; coenzyme Q10; methylsolanomethane (MSM); copper peptide (copper extract); plankton extract (phytosome); glycolic acid; kojic acid; ascorbyl palmitate; all-trans-retinol; azaleic acid; salicylic acid; broparoestrol; estrone; adrostenedione; androstanediols; etc. See U.S. Pat. No. 6,821,524. The steroids will generally be present at a concentration of less than about 2% of the total by weight of the composition, while the other skin benefit materials may be present at higher levels, for example as much as 10 to 15%.

The cosmetic compositions may further comprise sunscreens to lower skin's exposure to harmful UV rays. Sunscreens include those materials commonly employed to block ultraviolet light. Illustrative compounds are the derivatives of PABA, cinnamate and derivatives of salicylate (other than ferulyl salicylate). For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. Dermascreen may also be used. The exact amount of sunscreen employed in the compositions can vary depending upon the degree of protection desired from the sun's UV radiation. See U.S. Pat. No. 6,821,524.

Cosmetic Vehicles. It is contemplated that the peptides of the invention may further comprise a cosmetically acceptable vehicle to act as a dilutant, dispersant or carrier for the peptides, so as to facilitate distribution of the peptides when the composition is applied to the skin. Vehicles other than or in addition to water can include liquid or solid emollients, solvents, humectants, thickeners and powders. A cosmetically acceptable vehicle may comprise 5% to 99.9% by weight of the composition, and can, in the absence of other cosmetic adjuncts, form the balance of the composition.

The cosmetic compositions may be in the form of aqueous, aqueous/alcoholic or oily solutions; dispersions of the lotion or serum type; anhydrous or lipophilic gels; emulsions of liquid or semi-liquid consistency, which are obtained by dispersion of a fatty phase in an aqueous phase (OMI) or conversely (W/O); or suspensions or emulsions of smooth, semisolid or solid consistency of the cream or gel type. These compositions are formulated according to the usual techniques as are well known to this art.

When the compositions of the invention are formulated as an emulsion, the proportion of the fatty phase may range from 5% to 80% by weight, relative to the total weight of the composition. Oils, emulsifiers and co-emulsifiers incorporated in the composition in emulsion form are selected from among those used conventionally in the cosmetic or dermatological field. The emulsifer and co-emulsifier may be present in the composition at a proportion ranging from 0.3% to 30% by weight, relative to the total weight of the composition. When the compositions of the invention are formulated as an oily solution or gel, the fatty phase may constitute more than 90% of the total weight of the composition.

The compositions of the invention may also contain additives and adjuvants which are conventional in the cosmetic, pharmaceutical or dermatological field, such as hydrophilic or lipophilic gelling agents, hydrophilic or lipophilic active agents, preservatives, antioxidants, solvents, fragrances, fillers, bactericides, odor absorbers and dyestuffs or colorants. The amounts of these various additives and adjuvants are those conventionally used in the field, and, for example, range from 0.01% to 10% of the total weight of the composition. Depending on their nature, these additives and adjuvants may be introduced into the fatty phase, into the aqueous phase.

Exemplary oils which may be used according to this invention include mineral oils (liquid petrolatum), plant oils (liquid fraction of karite butter, sunflower oil), animal oils (perhydrosqualen(e), synthetic oils (purcellin oil), silicone oils (cyclomethicone) and fluoro oils (perfluoropolyethers). Fatty alcohols, fatty acids (stearic acid) and waxes (paraffin wax, carnauba wax and beeswax) may also be used as fats.

Emulsifiers which may be used include glyceryl stearate, polysorbate 60, PEG-6/PEG-32/glycol stearate mixture, and the like. Solvents which may be used include the lower alcohols, in particular ethanol and isopropanol, and propylene glycol.

Hydrophilic gelling agents include carboxyvinyl polymers (carbomer), acrylic copolymers such as acrylate/alkylacrylate copolymers, polyacrylamides, polysaccharides, such as hydroxypropylcellulose, natural gums and clays, and, as lipophilic gelling agents, representative are the modified clays such as bentones, fatty acid metal salts such as aluminum stearates and hydrophobic silica, or ethylcellulose and polyethylene.

An oil or oily material may be present, together with an emollient to provide either a water-in-oil emulsion or an oil-in-water emulsion, depending largely on the average hydrophilic-lipophilic balance (HLB) of the emollient employed. Levels of such emollients may range from about 0.5% to about 50%, by weight of the total composition. Emollients may be classified under such general chemical categories as esters, fatty acids and alcohols, polyols and hydrocarbons.

Esters may be mono- or di-esters. Examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms, such as cetyl, myristyl, palmitic and stearyl alcohols and acids. Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers. Exemplary hydrocarbons which may serve as emollients are those having hydrocarbon chains anywhere from 12 to 30 carbon atoms, such as mineral oil, petroleum jelly, squalene and isoparaffins.

Another category of functional ingredients within the cosmetic compositions of the present invention are thickeners. A thickener is typically present in amounts anywhere from 0.1 to 20% by weight of the composition. Exemplary thickeners are cross-linked polyacrylate materials available under the trademark Carbopol. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes.

In one aspect it is contemplated to use a mixture of sucrose esters of coconut fatty acids in aqueous ethanol solution. A mixture such as sucrose cocoate has been extensively used as a pharmaceutical excipient in cosmetic and dermatological products. With a hydrophilic and lipophilic value of 15, it has properties as a skin emollient and moisturizer. In vivo experiments using specific peptides showed that the most abundant sucrose ester in sucrose cocoate, sucrose monododecanoate, was an effective enhancer of peptide drug absorption (Ahsan et al., *Int. J. Pharm.* 251:95-203, 2003). The properties of these chemicals make sucrose cocoate an attractive candidate to serve as a possible absorption enhancer in the cosmetic formulation of the peptide compositions of the invention.

It is contemplated that the peptide compositions are formulated for use as day or night creams. Application areas include, but are not limited to, face, forehead, around the mouth, around the eye, area between the eyebrows, neck, decollete, hands.

Methods of Use. The compositions of the invention have widespread therapeutic utility to treat subjects in need. In one aspect, the subjects are mammalian subjects. In a related aspect, the subjects are human.

In one aspect, it is contemplated that the compositions of the invention inhibit neurotransmitter secretion. The compositions may act on the neuromuscular plate by blocking vesicular transport, which blocks neurosecretion of neurotransmitters such as norepinephrine, acetylcholine, and others.

In another aspect, it is contemplated that the compositions of the invention act to inhibit muscle contraction. In a related aspect, the compositions are used to reduce facial wrinkles caused by muscle contraction. For example, the composition may act on fibroblasts and myofibroblasts with contractile properties or act to inhibit actin filaments during muscle contraction. These peptides may inhibit the myosin troponin complex or kinases involved in contractile activity. It is contemplated that compositions comprising the peptides of the invention are applied to facial areas exhibiting wrinkles or prone to develop wrinkles, such as the area around the eyes, nose and mouth, to reduce the extent of wrinkles at these sites, prevent additional or deeper wrinkles from forming, or as a prophylactic agent to prevent wrinkling in these areas.

Additionally, the compositions could be used as short term myorelaxant in surgery like conotoxin peptides.

Further, the peptides can be applied as a myorelaxant on muscles by affecting muscle filament interaction and muscle contraction.

In a related aspect, the compositions may act to inhibit other types of muscle contraction. For example, the compositions of the invention may be use to treat dystonias, or movement disorders in which sustained muscle contractions cause twisting and repetitive movements or abnormal postures. The movements, which are involuntary and sometimes painful, may affect a single muscle, a group of muscles such as those in the arms, legs, or neck, or the entire body. Dystonias may be focal or multifocal dystonia, including, but not limited, to blepharospasm (forcible closure of the eyelids), and cranial dystonia (affects the muscles of the head, face, and neck). Treatments for these conditions may include administration of the peptides of the invention with other agents such as drugs that reduce the level acetylcholine. including trihexyphenidyl, benztropine, ethopropazine and procyclidine HCl. Drugs that regulate the neurotransmitter GABA may be used, including diazepam, lorazepam, clonazepam, and baclofen. Other agents that may be administered include those that act on dopamine, including levodopa/carbidopa and bromocriptine, pergolide, pramipexole requip (ropinerol), tetrabenazine, and reserpine.

Nondystonic conditions contemplated by the invention include hemifacial spasms, or tremors, such as those associated with Parkinson's disease. The peptides of the invention may be administered in conjunction with agents including, but not limited to, phenyloin, carbamazepine and clonazepam, to treat nondystonic conditions.

Compositions of the invention may also be used to treat general muscle spasm or spasticity, referring to a general upper motor neuron disorder characterized by a velocity-dependent increase in muscle tone. Spasticity can occur as the result of a variety of etiologies, including stroke, cerebral palsy, traumatic brain injury and multiple sclerosis. Disability resulting from spasticity includes pain, muscle spasm, reduced range of motion and impaired functional abilities. Medications for spasticity, such as baclofen, dantrolene and benzodiazepines may be administered in conjunction with peptides of the invention to treat these disorders or conditions.

The compositions of the invention are used to treat hyperhidrosis, or the condition of excessive sweating, including facial hyperhidrosis, axillary hyperhidrosis (sweating of the armpits), palmar hyperhidrosis (sweating of the hands), plantar hyperhidrosis, and sweating on the trunk area.

It is also contemplated that the compositions of the invention are useful to enhance wound healing. In wound healing the compositions may reduce the skin tension generated during repair of skin during wound healing and increase the rate of healing and reduce the amount of scarring.

It is further contemplated that the compositions of the invention are useful to accelerate muscle repair. In one aspect, the peptides of the invention interfere with fibrosis by interfering with TGF-β activity. Fibrosis is regulated by TGF-β which is first activated by a proconvertase such as furin.

The compositions of the invention are also used in a method for improving tissue turgor comprising the step of contacting a cell with an effective amount of the composition. In a related aspect, the invention provides a method for improving the appearance of the skin, the method comprising applying topically a cosmetic comprising a composition of the invention and a cosmetically acceptable vehicle.

It is contemplated that for therapeutic use, the compositions comprising one or more peptides of the invention may further comprise a second agent. It is contemplated that these agents may be given simultaneously, in the same formulation. It is further contemplated that the agents are administered in a separate formulation and administered concurrently, with concurrently referring to agents given within 30 minutes of each other.

In another aspect, the second agent is administered prior to administration of the composition of the invention. Prior administration refers to administration of the second agent within the range of one week prior to treatment with the composition of the invention, up to 30 minutes before administration of the composition of the invention. It is further contemplated that the second agent is administered subsequent to administration of the composition of the invention. Subsequent administration is meant to describe administration from 30 minutes after administration of the composition of the invention up to one week after administration of the composition.

For example, the compositions may comprise second agents useful as described herein above or below. For example, the compositions may comprise second agents useful in the treatment of the muscle contraction disorders described above. It is further contemplated that the compositions may comprise second agents which are neurotransmitter inhibitors, including but not limited to curare, α-bungarotoxin, conotoxin, alcuronium, gallamine, pancuronium, atracurium, vecuronium, Pirenzepine AF-DX 116 pF-HHSiD, ipratroprium, scopolamine and atropine.

The compositions may comprise second agents which are apoptosis inhibitors, including but not limited to, Chloromethyl Ketone (CMK), Fluoromethyl Ketone (FMK) (Morwell Diagnostics, Zurich, Switzerland), R(−)-Deprenyl-HCl, (−)-Huperzine A, Necrostatin-1, Anti-ARC (Apoptosis Repressor with Caspase Recruitment Domain) Caspasel/ICE inhibitor Z-WEHD, caspase-10 fmk inhibitor Z-AEVD, caspase-13 fmk inhibitor Z-LEED, caspase-2 fmk inhibitor Z-VDVAD, caspase-3 fmk inhibitor Z-DEVD, caspase-4 fmk inhibitor Z-YVAD, caspase-6 fmk inhibitor Z-VEID, caspase-8 fmk inhibitor Z-IETD, caspase-9 fmk inhibitor Z-LEHD, pan caspase fmk inhibitor such as Z-VAD and Z-VKD and pan caspase inhibitor OPH Q-VD.

The compositions or peptides of the invention may comprise second agents which are vasoconstrictors which acts to constrict blood vessels, including, but not limited to, ornipressin, norepinephrine, epinephrine, phenylephrine, naphazoline, oxymetazoline, antazoline, endothelin, thromboxane, and alpha-adrenergic agonists.

The compositions or peptides of the invention may comprise second agents which are anti-pain agents, including, but not limited to, lidocaine and derivatives, procaine, mexiletine, tocamide and flecamide, tetracaine, bensocaine, capsaicin, capzasin-P, menthacin, and zostrix.

The compositions or peptides of the invention may comprise second agents which are anti-inflammatory drugs including, but not limited to analgesics, including NSAIDs and steroids. Exemplary NSAIDs contemplated for use in the invention are chosen from the group consisting of ibuprofen, naproxen, Cox-1 inhibitors, Cox-2 inhibitors, and salicylates. Exemplary steroids contemplated include, but are not limited to, androgens, estrogens, progestagens, 21-aminosteroids, glucocorticoids, steroid neurotransmitters (neuroactive steroids) and other steroid hormones known in the art.

Also contemplated by the invention is a screening method comprising a neurosecretion assay useful to assess the effects of the peptides of the invention on neurosecretion as well as to identify other inhibitors of neurotransmitter release. The screening assay may also be useful to evaluate potential adverse effects of compositions of the invention.

In one aspect, the method of screening for an inhibitor of neurotransmitter secretion in a cell comprising: contacting a cell comprising a neurotransmitter with a candidate inhibitor; and detecting neurotransmitter release by determining the amount neurotransmitter released in the presence and in the absence of said inhibitor, wherein a decrease neurotransmitter release in the presence of said candidate inhibitor in comparison to the neurotransmitter release in its absence identifies the candidate as an inhibitor of neurotransmitter release. The peptides of the invention may be used as positive or negative controls for the assay, thereby determining if the candidate inhibitor acts similarly to the peptides of the invention.

Kits and Packaging. As an additional aspect, the invention includes kits which comprise one or more peptides or compositions of the invention packaged in a manner which facilitates their use to practice methods of the invention. In one embodiment, such a kit includes a compound or composition described herein (e.g., a composition comprising one or more peptides of the invention alone or in combination with a second agent, buffers, or a therapeutic compound), packaged in a container such as a sealed bottle or vessel, with a label affixed to the container or included in the package that describes use of the compound or composition in practicing the method. Preferably, the compound or composition is packaged in a unit dosage form. The kit may further include a device suitable for administering the composition according to a specific route of administration or for practicing a screening assay. Preferably, the kit contains a label that describes use of the compositions of the invention.

In another aspect, a small quantity of the cosmetic composition contemplated by the invention, for example from 1 to 100 ml, is applied to exposed areas of the skin, from a suitable container or applicator and, if necessary, it is then spread over and/or rubbed into the skin using the hand or fingers or a suitable device. The product may be specifically formulated for use as a hand, or as a facial treatment.

The cosmetic composition of the invention can be formulated as a lotion, a cream or a gel. The composition can be packaged in a suitable container to suit its viscosity and intended use. For example, a lotion or cream can be packaged in a bottle, or a propellant-driven aerosol device or a container fitted with a pump suitable for finger operation. When the composition is a cream, it can simply be stored in a non-deformable bottle or squeeze container, such as a tube or a lidded jar. The invention accordingly also provides a closed container containing a cosmetically acceptable composition as herein defined.

The following examples are provided to illustrate the invention, but are not intended to limit the scope thereof.

EXAMPLES

Example 1

Synthesis of L- and D-Peptides

Synthetic peptide sequences were prepared and characterized as described below. All amino acids used during the synthesis were L-amino acids or D-amino acids (Calbiochem-Novabiochem AG) as indicated in FIG. 1.

Peptide synthesis The peptides shown in FIG. 1 (SEQ ID NOs 1-23) were chemically synthesized by standard solid phase Fmoc chemistry on an Applied Biosystems 431A Peptide Synthesizer. The peptides were prepared using p-alkoxybenzylalkohol resin (Wang, Bachem, Switzerland). The synthesis was performed using a five-fold excess of Fmoc amino acid derivatives, DCCI and HOBt as activating agents and a 60 minute coupling time. Side chain protecting groups included: triphenylmethyl group for asparagines, glutamine, cysteine and histidine (Asn, Gln, Cys and His); pentamethylchroman-sulfonyl group for arginine (Arg); t-butyloxycarbonyl group for lysine and tryptophan (Lys and Trp); t-butyl group for aspartic acid, glutamic acid, serine, threonine and tyrosine (Asp, Glu, Ser, Thr and Tyr). The peptides were deprotected and cleaved from the resin by treatment with 2.5% H20, 5% triethylsilan in TFA for 2 hours at room temperature. After removal of the resin by filtration, the peptides were precipitated with tert-butyl methyl ether, centrifuged and the pellets resuspended in 50% acetic acid and lyophilized. The lyophilized material was then subjected to analytical HPLC and MALDI-TOF MS analysis.

Peptide Purification. Crude peptides were reconstituted in 1 ml 50% acetic acid in $H_2O$ and low molecular weight contaminants were removed by gel filtration on Sephadex G-25.

The materials eluted in the void volume were lyophilized, reconstituted in 1 ml 50% acetic acid in $H_2O$ and subjected to RP-HPLC on a Vydac column (250×22 mm, 10-15 µm). The column was eluted at a flow rate of 9 ml/min by a linear gradient of 0.1% TFA/acetonitrile on 0.1% TFA/$H_2O$, rising within 60 minutes from 10% to 100%. The optical density of the eluate was monitored at 220 or 280 nm. Fractions were collected and analyzed by MALDI-TOF. Fractions containing the peptide of the expected molecular weight were pooled and lyophilized. The purified material was then subjected to MALDI-TOF MS and analytical HPLC in a C18 nucleosil column (250×4 mm, 5 µm). The column was eluted at 1 ml/min by a linear gradient of acetonitrile on 0.1% TFA/$H_2O$, rising within 30 minutes from 0 to 60%. Detection was performed at 220 and 280 nm using a Waters 991 photodiode array detector.

Mass Spectrometry. α-cyano-4-hydroxycinnamic acid was purchased from Sigma (Sigma Chemical Co., St. Louis, Mo., USA). High performance liquid chromatography (HPLC)-grade trifluoroacetic acid was purchased from Fluka (Buchs, Switzerland), HPLC-grade $H_2O$ from Romil Ltd (Amman Technik SA, Kolliken, Switzerland) and acetonitrile was purchased from Biosolve Ltd (Chemie Brunschwig, Basel). All other chemicals were of highest purity and were used without further purification. MS analyses were performed using a Perseptive Biosystems MALDI-TOF Voyager DE-RP Mass Spectrometer (Framingham, Mass., USA) operated in the delayed extraction and linear mode.

Example 2

Synthesis of Retro-Inverso Isomers

Peptides of the invention may be all-D amino acid peptides synthesized in reverse to prevent natural proteolysis (i.e., all-D-retro-inverso peptides) (See U.S. patent publication 20050106695). An all-D retro-inverso peptide of the invention provides a peptide with functional properties similar to the native peptide.

The procedures for synthesizing a chain of D-amino acids to form the retro-inverso peptides are known in the art. See, e.g., Jameson et al., Nature 368:744-46, 1994; Brady et al., Nature 368, 692-93, 1994; Guichard et al., J. Med. Chem. 39:2030-39, 1996. Specifically, the retro-peptides are produced by classical F-moc synthesis and further analyzed by Mass Spectrometry as described above. They are purified by HPLC.

An exemplary retro inverso peptide was synthesized using Fmoc chemistry and the 9R-D peptide (GYGR-RRRRRRRG) (SEQ ID NO: 13) was replaced by the 9Rrev-D peptide (GRRRRRRRRGYG) (SEQ ID NO: 14).

Example 3

Assessment of Neurotransmitter Secretion

Differentiation and Neurotransmitter Secretion Assays. In order to assess the efficacy of the peptides of the invention on neurotransmitter secretion, a functional experimental model to study vesicular neurotransmitter release was first established.

The rat phaeochromocytoma (PC12) cell line, derived from a rat adrenal gland phaeochromocytoma [Greene et al., Proc Natl Acad Sci USA, 73: 2424-8, 1976], is commonly used as an in vitro model for both neurosecretory and neuronal cells (Greene et al., Proc Natl Acad Sci USA, 73:2424-8, 1976; Tischler et al., Lab Invest. 39:77-89, 1978). Since PC12 cells display vesicular catecholamine release upon stimulation (Chen et al., Am J Physiol, 266:C784-93, 1994) and uses the same conserved machinery that functions in synaptic neurotransmission (Burgoyne et al., Ann N Y Acad Sci, 710: 333-46, 1994; Burgoyne et al., Trends Neurosci, 18:191-6, 1995; Burgoyne et al., Bioessays, 20:328-35, 1998), the cells were chosen as model system for the neurosecretion assays.

Propagation and Culture of PC12 Cells. A large number of distinct PC12 cell lines are available. Many of these exhibit a propensity to aggregate and exhibit poor cell culture properties, including highly variable synthesis of acetylcholine and extreme heterogeneity across the culture, reviewed in [Martin et al., Methods Cell Biol. 71:267-86, 2003]. Therefore, a detailed characterization for desired properties of the PC12 cell line (PC12 ES) was conducted. Suitable growth conditions for this cell line were achieved as described below.

Differentiation of PC12 Cell Lines: Analysis of neurite outgrowth was conducted using PC12-ES cells as control. For both cell lines, differentiation was performed in the presence of nerve growth factor (NGF, 50 ng/ml) or the protein kinase inhibitor staurosporine (STSP, 100 nM) (Hashimoto et al., Exp Cell Res. 184:351-9, 1989; Hashimoto et al., J. Neurochem. 53:1675-85, 1989). Differentiation of the PC12-ES cells was assayed in complete Dulbecco's medium (DMEM-CM) and in DMEM high glucose supplemented only with 1% horse serum (DMEM-DM).

To examine the differentiated morphology of PC12 cell lines in the presence of NGF or STSP, the cells were monitored by phase contrast microscopy and pictures were taken at different intervals after addition of the differentiation inducers (1-7 days). PC12-ES cells differentiated efficiently after induction with STSP. Cells developed neurites within 24 hours in DMEM-CM medium or 48 hours in DMEM-DM. PC12-ES terminal differentiation was also observed after 24 h of nerve growth factor (NGF) addition but only in DMEM-DM. PC12-ES cell line differentiated to completion in serum free medium in response to NGF (2-3 days). Nevertheless, the NGF effect on the cells was slower in complex medium (4-5 days). Neurite outgrowth was not observed in the control samples, without addition of NGF or STSP. These results demonstrate that untreated PC 2 cells continue to divide and do not differentiate, maintaining a round morphology and no neurite extensions.

Neurotransmitter Secretion by PC12-ES. PC12 cells offer a number of advantages for studies of regulated secretion. Exocytosis of large dense-core vesicles (LDCVs) in these cells can be easily assayed for the release of radioactive norepinephrine ([$^3$H]NE) from pre-labeled cells [Greene et al., *Brain Res*, 129:247-63, 1977; Greene et al., *J Neurochem*, 30:579-86, 1978; Greene et al., *J. Neurochem.* 30:549-55, 1978; Greene et al., *Brain Res.* 138:521-8; 1977; Greene et al., *Nature* 268:349-51, 1977]. The neurosecretion assay was carried out by measuring [$^3$H]NE evoked secretion with PC12-ES cells. Different secretion buffers were tested (e.g., calcium secretion buffer CaSB and CaSB-Glucose) and secretagogues (Potassium, 80 mM; Nicotine, 0.1 mM; or Carbachol, 1 mM; see Table 1), defined as an agent that causes or stimulates secretion. [$^3$H]NE evoked secretion was assayed with non-differentiated PC12 cells as well as NGF or STSP differentiated cells.

PC12-ES cells were either untreated, treated with STSP (100 nM), or treated with NGF (50 ng/ml) for 48 h before the loading with [$^3$H]NE and prepared for release measurements. The cells were then stimulated for 15 minutes with either potassium (80 mM), nicotine (0.1 mM), or carbachol (1 mM). Media were collected, and released [$^3$H]NE as well as the total cell content were determined by liquid scintillation counting. Basal secretion was measured in calcium secretion buffer (CaSB) without secretagogue or CaSB supplemented with 11 mM glucose (CaSB-Glucose). The data are expressed in Table 1 as the percent secretion: [amount released/(amount released+amount in cell lysate)]×100. Net secretion is secretagogue-stimulated release minus basal release.

There was a considerable evoked release of [$^3$H]NE (Table 1) and these results are consistent with published reports (Avila et al., *Mol. Pharmacol.* 64:974-86, 2003). Under all tested conditions, the percentage of released [$^3$H]NE was detectable. Undifferentiated cells exhibit lower loading with [$^3$H]NE than differentiated cells, and as main disadvantage, these cells are non-responsive to natural neurotransmitter secretion inhibitors such as Botulinum neurotoxins. Therefore, future experiments were performed with differentiated PC12-ES cells.

TABLE 1

| Secretagogue | Non-differentiated cells | NGF differentiated cells | STSP differentiated cells |
|---|---|---|---|
| CaSB | 9.5% | 14% | 21.7% |
| CaSB-High K$^+$ | 42% | 24% | 44.3% |
| CaSB-Nicotine | 40.3% | 21% | 47.8% |
| CaSB-Carbachol | 44.7% | 27% | 46.5% |
| CaSB-Glucose | 21.3% | 12% | 18.5% |
| CaSB-Glucose High K$^+$ | 46.5% | 15.9% | 48.5% |
| CaSB-Glucose Nicotine | 32.8% | 33.6% | 47.8% |
| CaSB-Glucose Carbachol | 37.24% | 32.4% | 57% |

Example 4

Inhibition of Neurosecretion

Using the neurosecretion assay described above, peptides fused to the TAT-PTD (L-TAT) were tested for inhibition of neurotransmitters and compared to use of L-TAT alone (SEQ ID NO: 3). In vitro screening for synthetic peptides capable of efficiently and selectively blocking neurotransmitter release in the PC12 cell line grown under defined conditions was performed.

For this assay, published synthetic peptides that mimic the amino acid sequence of segments from synaptotagmin, SNAPs and SNAP-25 [L-Tat-ESUP-A (SEQ ID NO: 1) and acetyl-L-Tat-hexapeptide (SEQ ID NO: 2)], were used. These peptides are known to arrest $Ca^{2+}$-dependent secretion from chromaffin cells by inhibiting vesicle docking.

PC12 cells were washed with DMEM-WM (Dulbecco's Modified Eagle Medium (GIBCO cat. no. 31968) completed with 25 units of penicillin and streptomycin each) and loaded for 1-2 h with [$^3$H] norepinephrine (NE; 0.5 μCi/ml) in DMEM-CM (DMEM-WM complemented with 6% horse serum and 6% fetal calf serum). Cells were washed for 1 h with DMEM-WM, and then washed 2 times at 5-minute intervals. Basal release was determined by a 15-minutes incubation with CaSB-glucose 5 mM $K^+$ (CaSB-glucose: 140 mM NaCl, 5 mM KCl, 2 mM $CaCl_2$, 11 mM glucose, [pH 7.4]). The peptides were added to the cells at defined concentrations after loading with NE but before induction of secretion. Cells were depolarized with 85 mM $K^+$ (CaSB-glucose with $Na^+$ reduced accordingly) for 15 minutes to determine stimulated release. Superfusate (1 ml) was removed to tubes. Adherent cells were solubilized in CaSB-glucose-0.1% Triton (1 ml/well). The quantities of released and non-released radiolabeled neurotransmitter were determined by liquid scintillation counting of cleared superfusates and cell lysates, respectively. Total uptake was calculated by addition of released and retained radioactivity, and the percentage release was as calculated (released counts/total uptake counts)×100. Results were also expressed as percent inhibition of neurosecretion.

Culture with the L-TAT-ESUP-A, L-Tat, L-Tat-hexapeptide exhibited a dose dependent inhibition of PC12 neurotransmitter secretion as shown in Table 2 below. ESUP-A alone showed only minimal inhibition.

TABLE 2

| Peptide | L-Tat-ESUP-A | L-Tat | L-Tat-Hexapep | ESUP-A |
|---|---|---|---|---|
| 10 μM | 30% | >20% | <10% | NA |
| 50 μM | 40% | 50% | <35% | NA |
| 100 μM | 50% | 55% | >50% | 20% |
| 250 μM | 70% | 70% | 60% | NA |

Because L-Tat was shown above to be an efficient inhibitor of neurotransmitter release, the effect of the D-analog D-Tat (SEQ ID NO: 12) on PC12 neurosecretion was also tested. Both L- and D-Tat peptides showed a noticeable inhibition of neurotransmitter-evoked secretion by the PC12 cells, inhibiting approximately 50 to 55% of secretion. Additional peptides were tested and the inhibition was demonstrated as follows: 9R-L (SEQ ID NO: 5) approximately 70% inhibition, 9K-L (SEQ ID NO: 6) approximately 20% inhibition, 9R-D (SEQ ID NO: 13) approximately 65% inhibition, 9Rrev-D (SEQ ID NO: 14) approximately 57% inhibition, 9R-L-Ac-am (SEQ ID NO: 11) approximately 67% inhibition.

Except for ESUP-A, all of the peptides tested showed a noticeable inhibition of neurotransmitter-evoked secretion by the PC12 cells. However, the peptide L-Tat (SEQ ID NO: 3) exhibits more than 60% inhibition of the evoked neurosecretion even when used alone. This result is not expected and was not reported before even when L-Tat was extensively used as an efficient transducing domain.

The stability of the L-Tat and D-Tat peptides was tested over a period of 48 hours to determine the continued presence of the peptide on the inhibition of neurosecretion by PC-12 cells. The neurosecretion assay was performed as above with L-Tat, D-Tat, and L-Tat 49-86 (SEQ ID NO: 4) incubated at 100 µM and MRPEDpep (SEQ ID NO: 7) (100 µM). Inhibition of secretion is shown in Table 3.

TABLE 3

| Time | L-Tat | D-Tat | L-Tat 49-86 | MRPEDpep |
|---|---|---|---|---|
| No Serum | 65% | 35% | 50% | 17% |
| 0 hours | 50% | 40% | <20% | >20% |
| 1 hour | 38% | 50% | >10% | 23% |
| 24 hours | 35% | 45% | 26% | 15% |
| 48 hours | 39% | 45% | 25% | NA |

Further assessment of the stability of the peptides 9R-D, 9Rrev-D, 9R-L/Ac-Am, and 9R-L cultured with PC12 cells for 48 hours in the presence or absence of serum indicates that all these peptides maintain levels of inhibition of approximately 80%, and up to 90%, over the 48 hour period, indicating good stability of the peptides in culture.

None of the above peptides exhibited any significant cytotoxic effects on PC12 cells as measured by MTT assay. Very little toxicity was present at 24 hours, and cytotoxicity at 48 hours was only slightly greater than at 24 hours. Cytotoxicity generally dipped to approximately 90% live cells when peptides were administered at 500 µM.

Additional peptides such as MRP (SEQ ID NO: 7), L-Tat-MRP (SEQ ID NO: 9), 3D-MRP (SEQ ID NO: 8), L-Tat-3D-MRP (SEQ ID NO: 10), were assessed for inhibition of neurosecretion by PC12 cells. FIG. 2 shows dose dependent inhibition of neurosecretion by all peptides tested. These results also demonstrate that attachment of L-Tat to either the MRP or the 3D-MRP peptides significantly improves inhibition of neurosecretion from cells.

L-Bel1 (same sequence as L-Tat), its D-amino acid-substituted analog (D-Bel1), and L-Bel2 (same as L-Tat 49-86) were tested in the assay alone and in conjunction with L-Tat and other peptides previously assayed.

Figure 3:
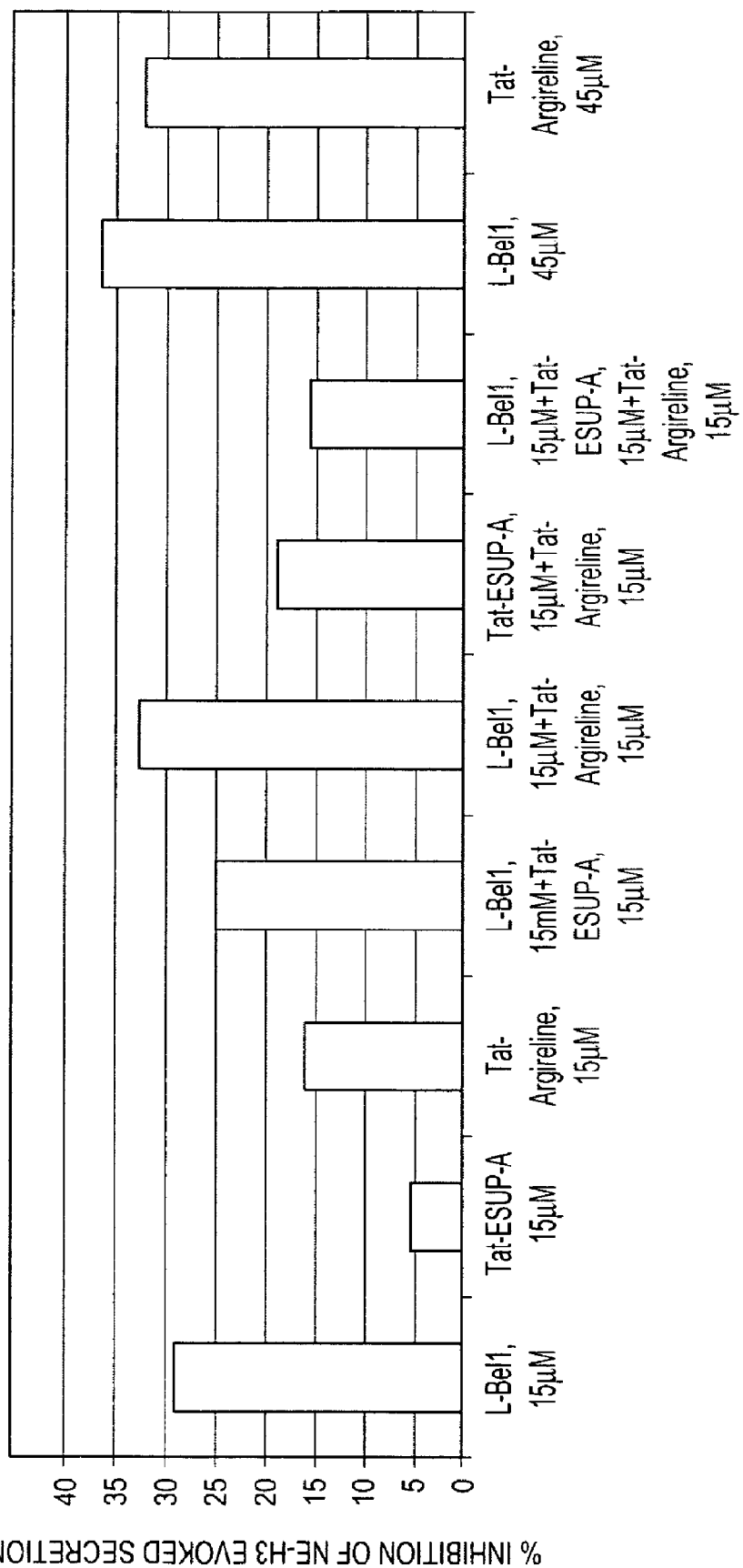
FIG. 3 shows inhibition of neurosecretion of PC12 cells by combinations of peptides of the invention.

ESUP-A (25 µM) cultured in combination with L-Tat (25 µM) improved the inhibition by ESUP-A slightly, but there was no synergistic effects of L-Tat with argireline (25 µM). The peptide L-Bel1 at 100 µM was a potent inhibitor and exhibited more than 60% inhibition of the evoked neurosecretion. Remarkably L-Bel1 enhanced the potency of some peptides showing a very small inhibitory effect such as ESUP-A (FIG. 3). The results also demonstrated that the inhibitory effect of L-Bel1 is dose dependent. Furthermore, L-Bel1 has no marked cytotoxicity on PC12 cells as demonstrated by a MTT proliferation assay. L-Bel1 is very stable in serum and in presence of PC12 cells in an in vitro assay. Similarly the D-Bel1 is also functional.

Further analysis was performed comparing the inhibitory effects of 9R-D alone, 9R-MRP (SEQ ID NO: 22) with 9R-D mixed with L- or D-Argireline. Culture of cells with the peptide 9R-D (50 µM), the fusion peptide 9R-MRP (50 µM) or 9R-D mixed with D-Argireline (50 µM each), all inhibited secretion by approximately 70%. Peptide 9R-D (50 µM) demonstrated approximately 75% inhibition while 9R-D mixed with Argireline (25 µM each) demonstrated approximately 65% inhibition. Both L-Argireline (50 µM) or D-Argireline (50 µM) demonstrated no inhibition of neurosecretion by cells.

These results show that several of the peptides described herein are highly efficient neurotransmitter release inhibitors, e.g., L-Bel1 (L-Tat), its D-analog (D-Bel1). These peptides provide useful agents for inhibition of neuropeptide secretion and may provide useful treatments to inhibit neurotransmitters in patients, for example, to treat muscle contractions, wrinkles and other conditions associated with neurotransmitter release.

Example 5

Basic Synthetic Peptides are Potent Inhibitors of the Preproconvertase Family

Members of the subtilisin-like proprotein/prohormone convertase (PC) family play a central role in the processing of various protein precursors ranging from hormones and growth factors to bacterial toxins and viral glycoproteins. Proteolysis occurring at basic amino acid residues is mediated by basic amino acid-specific proprotein convertases, including: PC1/3, PC2, furin, PACE4, PC4, PC5/6, and PC7. In contrast, proteolysis at non basic residues is performed by the subtilisin/kexin-like isozyme-1 (SKI-1/S1P) and the newly identified neural apoptosis-regulated convertase-1 (PCSK9/NARC-1). In addition to their requirement for many physiological processes, these enzymes are also involved in various pathologies such as cancer, obesity, diabetes, lipid disorders, infectious diseases, atherosclerosis and neurodegenerative diseases (Scamuffa, et al. FASEB J. 20:1954-63, 2006). These PC enzymes can act on various substrates such as synaptotagmin or on growth factors such as TGF-β.

Furin has been demonstrated to process many pro-proteins, including TGF-β, BMP-4, pro-α-NGF, Notch1 receptor, HIV gp160, and several metalloproteinases (Dubois et al., Am J Pathol 158:305-316, 2001). Overexpression of TGF-β is associated with the development of fibrosis, possibly by inhibiting matrix proteins degradation and increasing expression of collagen (Dubois et al, supra).

To determine if the peptides described herein have an effect on the activity of PC enzymes which are involved in a condition or disorder such as fibrosis, the effect of the peptides on furin activity in vitro was measured as percent inhibition of cleavage of the furin substrate fluorogenic t-butyloxycarbonyl (Boc)-RVRR-7-amino-4-methylcoumarin (MCA).

All in vitro enzyme studies were performed at room temperature in a final volume of 50-100 μl in 96-well flat-bottom black plates. The buffer consisted of 100 mM HEPES, 1 mM $CaCl_2$, 0.5% TritonX-100, and 1 mM 2-β-mercaptoethanol pH 7.5. Assays were performed using Boc-RVRR-MCA as fluorogenic substrate at 100 μM. Recombinant furin (0.8 U of activity) was incubated with Boc-RVRR-MCA in the presence or absence of varying concentrations of synthetic peptides D-9Rac/am (SEQ ID NO. 15), L-Bel1 (SEQ ID NO. 3), or L-9K (SEQ ID NO. 6). One unit of activity is defined as the amount of furin that can release 1 μmol of MCA from the fluorogenic Boc-RVRR-MCA per min at 30° C. The release of highly fluorescent 7-amino 4-methyl coumarin (MCA) from the Boc-RVRR-MCA was monitored by a spectrofluorometer instrument at excitation and emission wavelengths of 370 nm/460 nm. For measurement of $K_{i(app)}$ values, the inhibitor concentrations were varied over a range wide enough to yield residual activities of 25-75% of the control value.

Figure 4A:
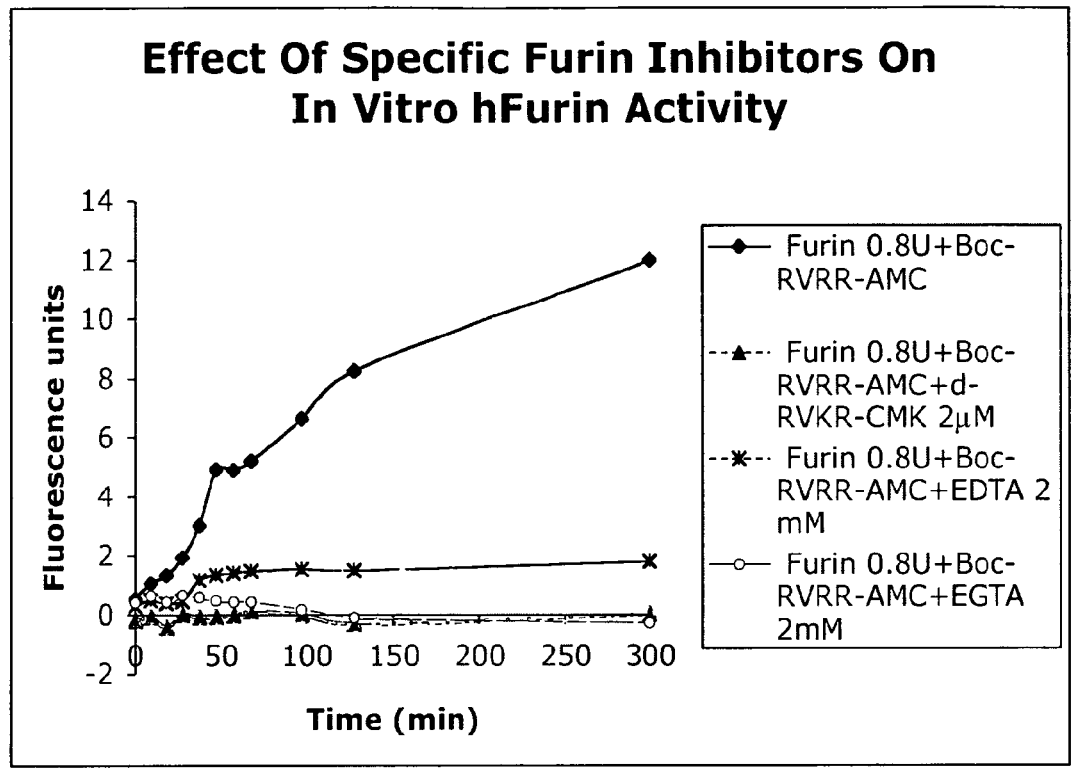
FIG. 4A shows the effect of furin inhibitors on furin activity in vitro.

These experiments showed that that furin activity is inhibited by the specific furin inhibitor Decanoyl (d) -RVKR-chloromethylketone (CMK) (CALBIOCHEM) (FIG. 4A). In addition, the chelators EDTA and EGTA effectively suppressed furin activity. These results are consistent with other data showing that furin is $Ca^{2+}$ dependent cellular endoprotease.

Figure 4B:
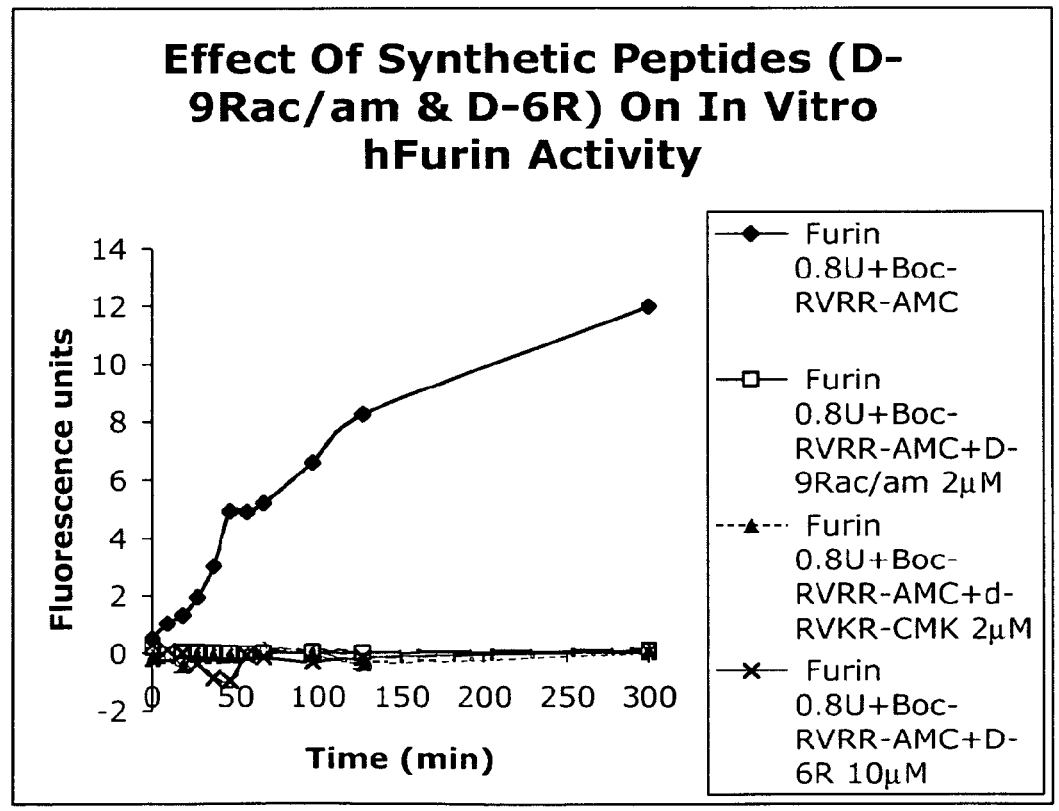
FIG. 4B shows the effect of synthetic peptides on furin activity in vitro.
Figure 5A:
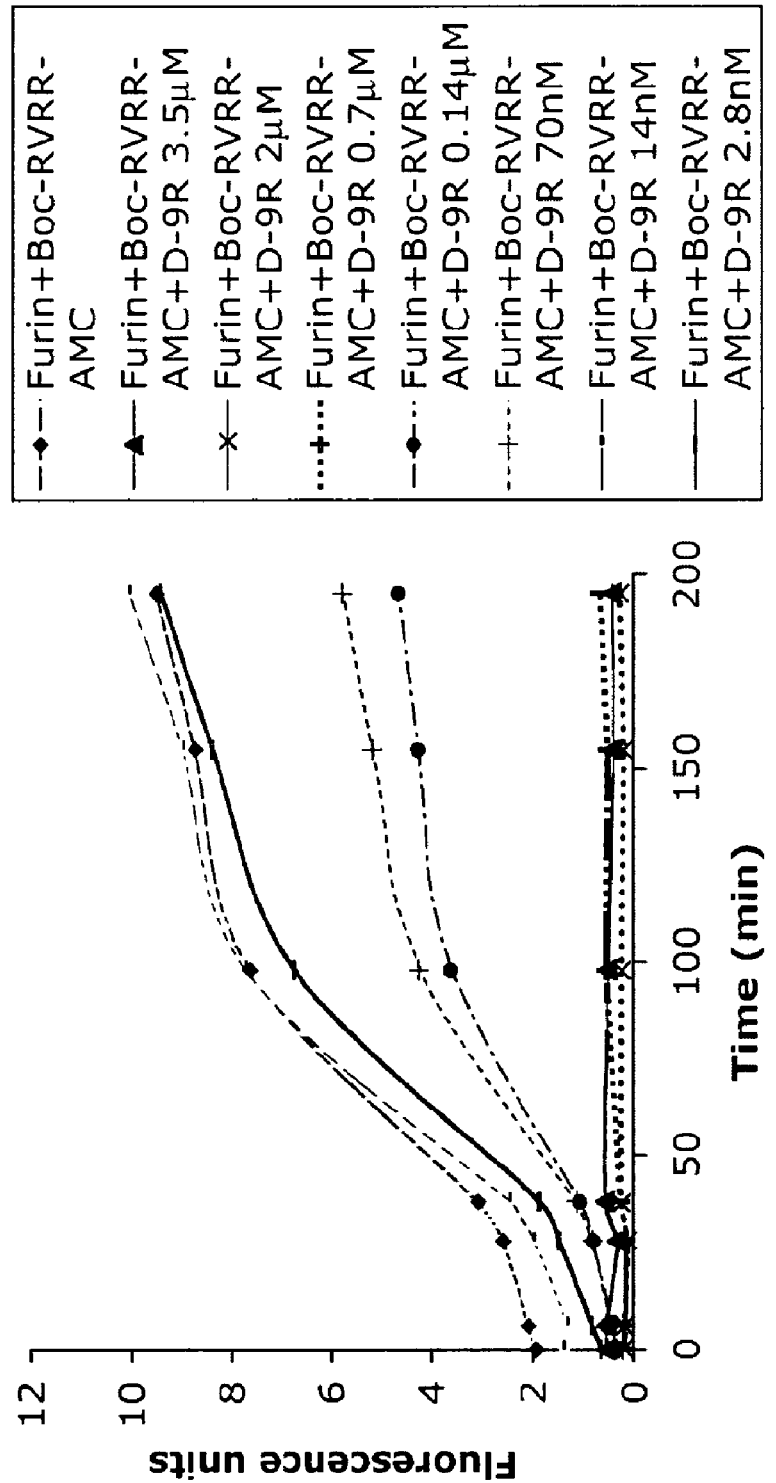
FIG. 5A depicts the effect of varying concentrations of the 9Rac/am peptide on furin activity.
Figure 5B:
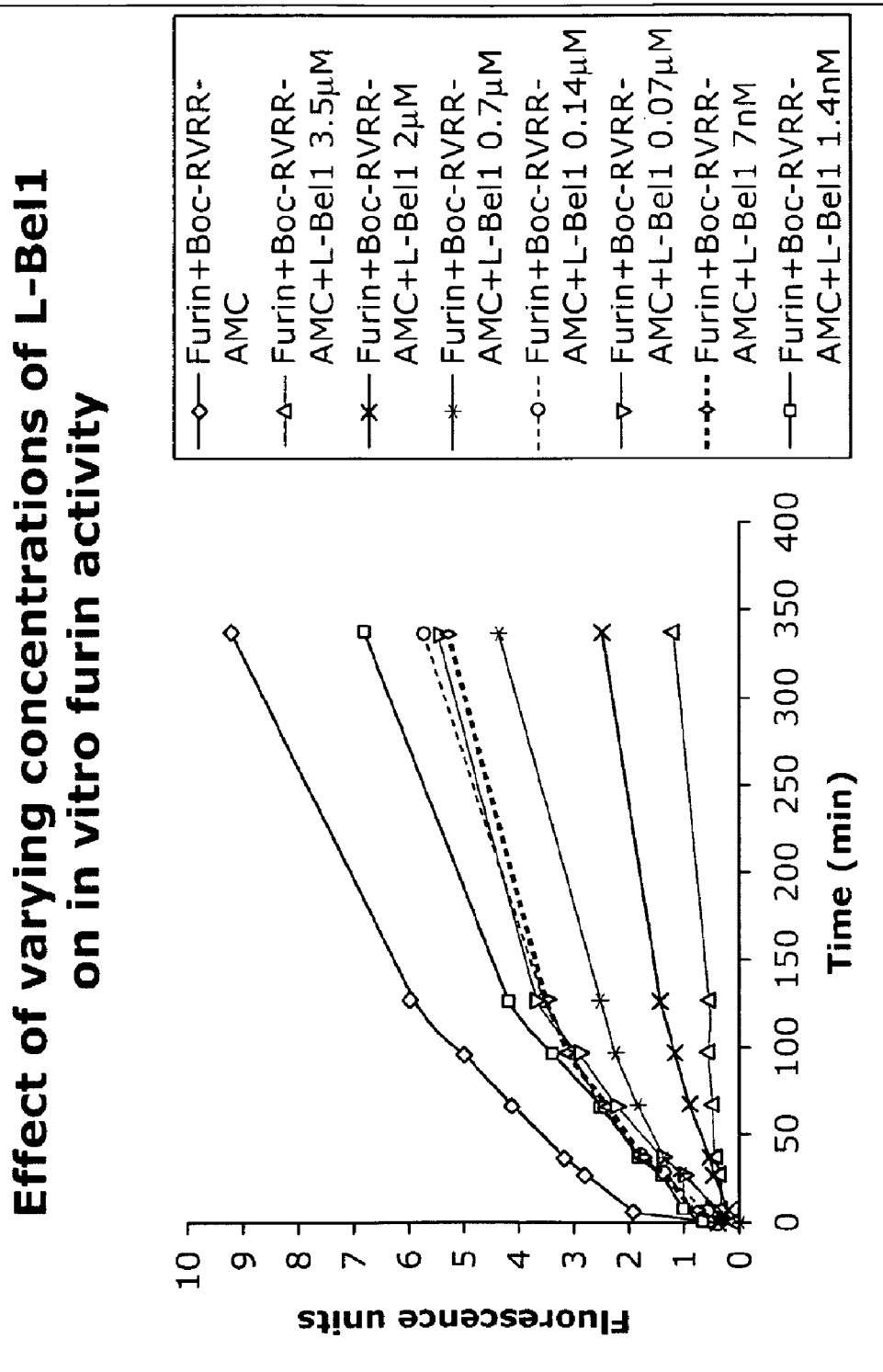
FIG. 5B shows the effects of varying concentrations of L-Bel1 peptide on furin activity.
Figure 5C:
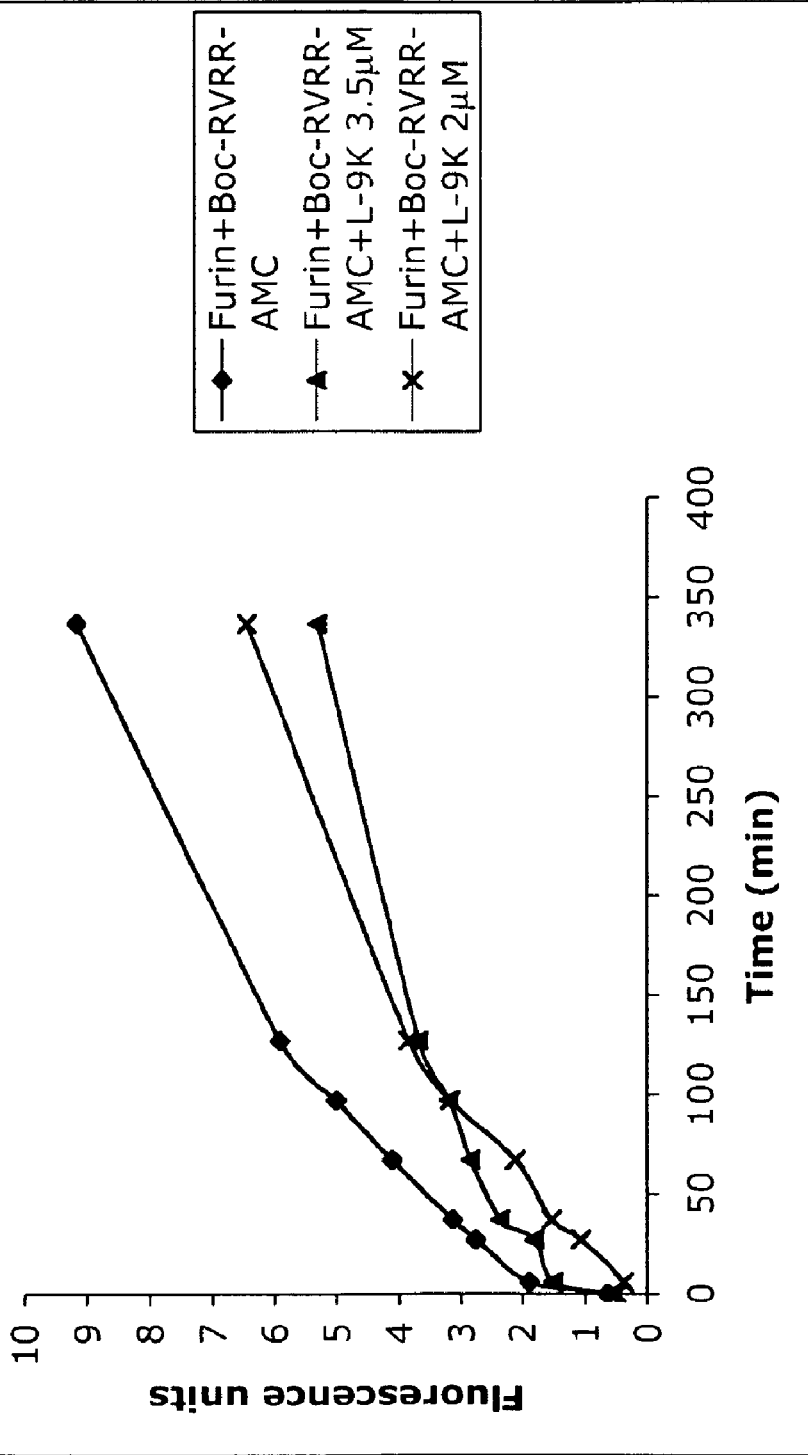
FIG. 5C shows the effect of L-9K on furin activity.

Many of the synthetic peptides described herein (see e.g., FIG. 1, SEQ ID NO. 1 TO SEQ ID NO. 23) are potent PC inhibitors and exhibit greater specificity to furin. As demonstrated in FIG. 4B the basic peptides including D-9Rac/am (SEQ ID NO. 15), D-6R (SEQ ID NO. 19), and L-Bel1 (SEQ ID NO. 3) inhibited to completion in vitro furin activity ($K_i$ in nM) when compared against Boc-RVRR-MCA as substrate. D-9Rac/am (SEQ ID NO. 15) appears to be more effective inhibitor than all the peptides tested (FIG. 5). Thus while 0.7 μM of D-9Rac/am is sufficient to fully block the cleavage of Boc-RVRR-CMA by furin (FIG. 5A), L-Bel1 and L-9K required a higher amount (3.5 μM and >3.5 μM respectively) for complete blockade of this cleavage (FIGS. 5B and 5C). D-9Rac/am showed a $K_{i(app)}$=170 nM compared to $K_{i(app)}$= 370 nM for L-Bel1 and to Ki=1 nM for FI-I (CALBIOCHEM). Thus, D-9Rac/am is the strongest furin inhibitor tested in these conditions.

Example 6

Basic peptides Inhibit Intracellular Furin Activity

Experiments described above showed that certain synthetic peptides could effectively inhibit furin activity in an enzyme-substrate assay. However, it is useful to determine if the peptides have the same effect on furin activity in a cellular environment, by assaying activity in PC12-ES cells which express furin.

To monitor the intracellular furin activity, 80% confluent PC12-ES cells were washed twice with ice-cold phosphate-buffered saline (PBS1×) by centrifugation at 800×g for 5 minutes at 4° C., resuspended in 100 mM HEPES, 1 mM $CaCl_2$, 0.5% TritonX-100, and 1 mM 2-β-mercaptoethanol, pH 7.5, sonicated 6 times at 4° C. for 10 seconds, and then centrifuged at 8000×g for 20 minutes at 4° C. The protein concentration in the samples was determined using a bicinchonic acid protein assay kit (Pierce Chemical Co.).

Intracellular furin activity was measured with a furin-specific fluorogenic substrate, t-butyloxycarbonyl (Boc)-RVKR-7-amino-4-methylcoumarin (MCA). Briefly, the cell lysate (20 μg-60 μg of protein) prepared as described above was incubated with 100 μM Boc-RVRR-MCA in a 96-well flat-bottom black plate for at least 6 hours at room temperature and fluorescence measured by excitation at 365 nm and emission at 450 nm.

Figure 6C:
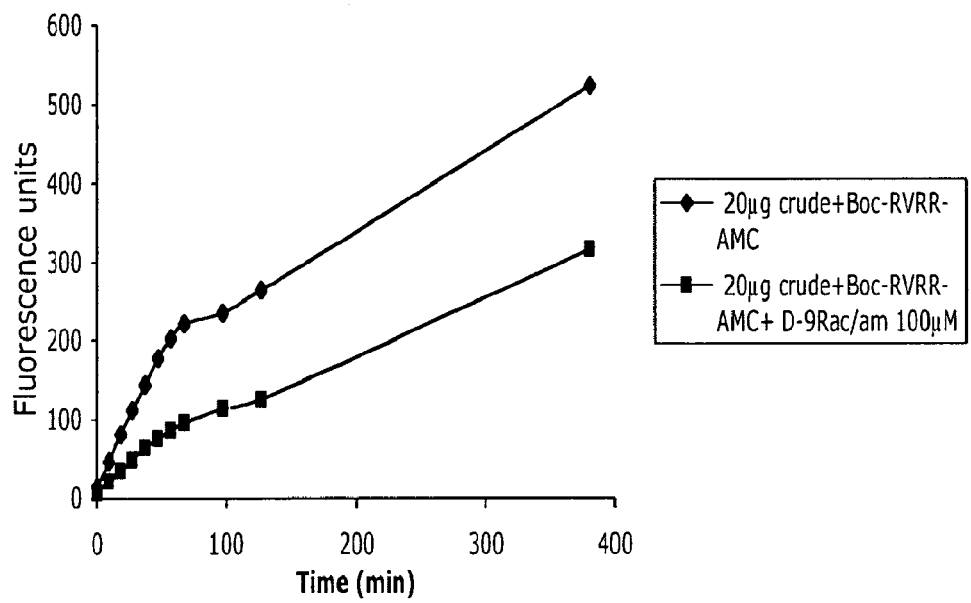
FIG. 6C, peptide D-Rac/am.
Figure 6D:
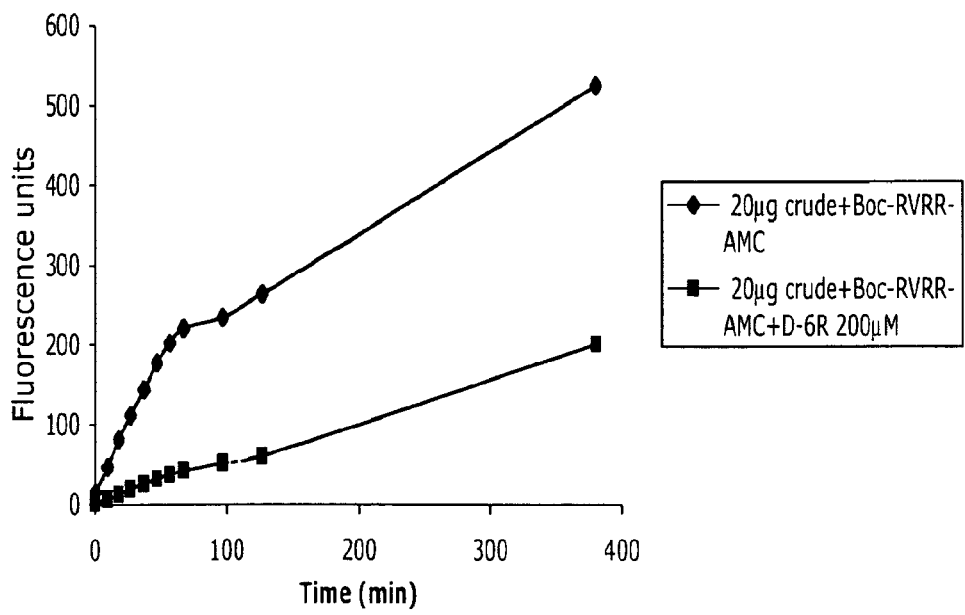
FIG. 6D, peptide D-6R) on furin activity in PC12-ES cells.

Furin activity was constitutively detected in PC12-ES cells (FIG. 4). Culture of PC12-ES cells with various furin inhibitors showed that intracellular furin activity is inhibited by high concentrations of EDTA (50 mM), EGTA (50 mM) (FIG. 6A), and the furin synthetic inhibitor Dec-RVKR-CMK (50 μM, CALBIOCHEM) (FIG. 6B), indicating that the enzymatic activity detected was substantially that of furin. Further, furin activity is blocked by both D-9Rac/am (100 μM) (FIG. 6C) and D-6R (200 μM) (FIG. 6D). Only 100 μM of D-9Rac/am (SEQ ID NO. 15) was needed to block the intracellular furin activity measured in cell lysate compared to 200 μM of D-6R (SEQ ID NO. 19). Thus, similar to the enzyme/substrate assays above, D-9Rac/am (SEQ ID NO. 15) appears to be more effective inhibitor than D-6R (SEQ ID NO. 19) in inhibiting furin.

Example 7

Effects of Synthetic Furin Inhibitors and Arginine Rich Peptides on Neurosecretion Using the neurosecretion assay described in Example 3 above the effect of the synthetic furin inhibitor Decanoyl-Arg-Val-Lys-Arg-CMK (FI-I, CALBIOCHEM) on neurotransmitter secretion was evaluated. FI-I is a peptidyl chloromethylketone that binds to the catalytic site of furin and blocks its activity. Hence, it can be used as a high specificity cleavage inhibitor of viral glycoproteins and blocker of viral replication (Sugrue, et al. *J. Gen. Virol.* 82:1375-86, 2001; Wang, et al. *J. Biol. Chem.* 276:35953-60, 2001).

Briefly, undifferentiated PC12-ES cells were loaded with [$^3$H]NE and prepared for evoked release measurements. The cells were then stimulated for 15 minutes with potassium (80 mM)+/−the specific furin inhibitor or synthetic peptides. Media were collected, and released [$^3$H]NE as well as the total cell content were determined by liquid scintillation counting. Basal secretion was measured in calcium secretion buffer supplemented with 11 mM glucose (CaSB-Glucose). The data are expressed in Table 4 as the percent secretion= [amount released/(amount released+amount in cell lysate)]× 100. Net secretion is secretagogue-stimulated release minus basal release.

FI-I showed a remarkable inhibition of neurotransmitter-evoked secretion by the PC 2-ES cells. When used at 100 μM FI-I exhibits 50% inhibition of secretion as compared to 76.2% inhibition for D-9Rac/am and 57.4% for D-6R (Table 4).

TABLE 4

Effect of FI-I on evoked neurotransmitter secretion by PC12-ES cells

| [Peptide] μM | D-9Rac/am | D-6R | L-Bel1 | FI-I |
|---|---|---|---|---|
| 10 | 52.4% | 39.6% | 24.6% | 12.6% |
| 100 | 76.2% | 57.4% | 56.4% | 50% |

This inhibition effect is dose dependent as demonstrated in Table 4. Furthermore, FI-I has no marked cytotoxicity on PC12-ES cells as demonstrated by a MTT proliferation assay.

Example 8

Subcellular Localization and Colocalization of Peptides and Furin

Two peptides of interest were FITC-labeled (Anaspec) to follow their interiorization on PC-12 cells (rat pheochromocytoma cells): L-Bel1 (SEQ ID NO. 3) and D-9Rac/am (SEQ ID NO. 15). After observation of L-Bel1-FITC conjugate interiorization, a monoclonal antibody for furin endoprotease was used for colocalization studies by confocal microscopy analysis.

PC-12 cells were resuspended in Dulbecco's modified Eagle's medium (DMEM) high glucose (Gibco BRL, Life Technologies) containing 6% decomplemented horse serum, 6% decomplemented fetal bovine serum, supplemented with 25 U/ml penicillin-streptomycin-I-glutamine. Cells were seeded at $3\times10^4$ cells/well (200 µl), on 8-well microscope slide chamber (BD Biosciences), previously coated with collagen I (Roche Diagnostics) solution (0.0007%). After an overnight incubation at 37° C. in 5% $CO_2$, cells were washed twice using fresh medium without serum, and then incubated in the presence or absence of the peptide, for the indicated time. Cells were then washed twice using 2% BSA/PBS solution, and fixed with 3% paraformaldehyde solution at room temperature for 10 minutes. Again, cells were washed twice and then permeabilized with saponin buffer (0.1% saponin, 2% BSA, 10 mM HEPES in PBS) at room temperature for 10 minutes. Cells were incubated with a monoclonal antibody for furin endoprotease, washed twice with 2% BSA/PBS solution, and incubated with a secondary antibody anti-mIgG-Alexa red. Both incubations were done at room temperature for 1 hour. When indicated, cells were treated with DAPI dihydrochloride (0.02 µg/ml), at room temperature for 10 minutes, for nuclear staining. A last washing step was done twice with cold PBS, and the chamber upper part was detached using the removal device. Slides were mounted and sealed, and stored at 4° C. in the dark until confocal microscopy analysis.

The fluorescent images were obtained by confocal laser scanning microscope (Zeiss LSM 510) with lasers of argon (488 nm), helium-neon 1 (543 nm), and enterprise (364 nm); connected to an inverted fluorescence microscope (Zeiss Axiovert 100 M), equipped with a 63×/1.4 PL APO chromate objective lens. The fluorescence emitted was selected by a group of filters and exhibited with a resolution of 512×512 pixels by RGB.

Figure 7A:
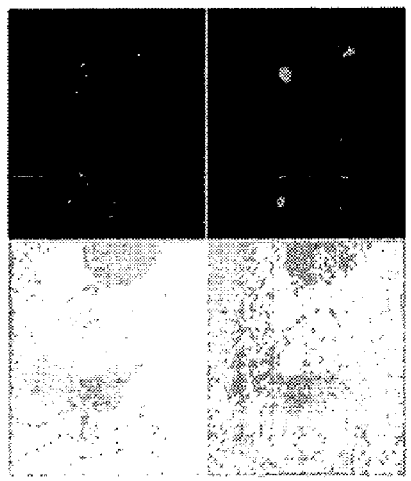
Figure 7B:
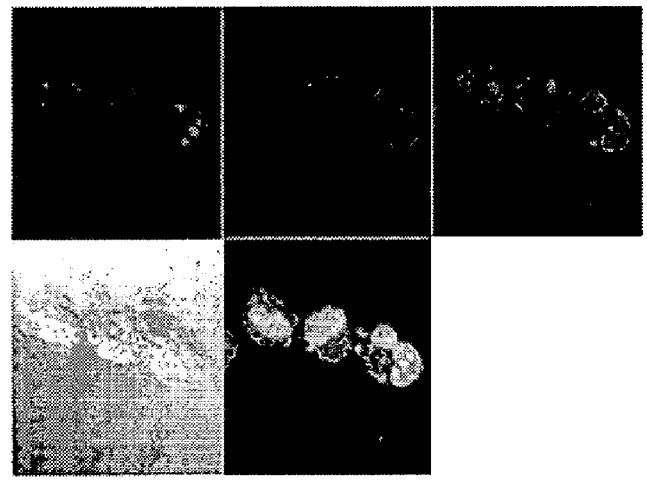
FIG. 7B shows staining of L-Bel1 and anti-furin antibody.

The FITC-labeled peptide L-Bel1 crosses the basal membrane of PC12 cells at all concentrations tested, (1 and 100 µM). FIG. 7A depicts LBel-1 staining alone and FIG. 7B shows L-Bel1 and furin staining of PC-12 cells. Staining shows that peptide internalization gives rise to cytoplasmic punctuated signals after 2 minutes of incubation, but evolves into a nuclear, and mainly nucleolar, staining pattern after 10-30 minutes of treatment. The furin endoprotease staining showed cytoplasmic punctuated structures, probably identifying the immature secretory granules containing this enzyme (FIG. 7B).

Preliminary experiments with cells double-stained with FITC-Bel1 and anti-furin antibody-Alexa red showed no colocalization, even though both molecules present a cytoplasmic localization (FIG. 7B). Further assays using specific markers for secretory vesicles may be done to more accurately colocalize the proteins.

Example 9

Effect of Peptides on Actin Cytoskeleton Organization

As demonstrated above, synthetic peptides of the invention are internalized into cellular vesicles. F-actin plays a central role in directing vesicle and protein traffic and in cytoskeletal rearrangement. Based on the association of actin with vesicle transport and the internalization of peptides in vesicles, the effect of the peptides on actin cytoskeleton organization was measured.

Slides with PC-12 cells were prepared as stated previously for localization studies. Briefly, cells were exposed to FITC-labeled or unlabeled peptides, at various concentrations, for 30 minutes, fixed and then permeabilized. Subsequently, F-actin was fluorescently labeled with phalloidin-Tetramethyl Rhodamine Iso-Thiocyanate (TRITC) (Sigma Aldrich) conjugate, diluted on saponin buffer (0.25 µg/ml), and nuclear staining with DAPI dihydrochloride (Sigma Aldrich) (0.02 µg/ml), at room temperature for maximum 30 minutes. Finally, slides were mounted and sealed, and stored at 4° C. protected from light. The effect of the peptides to actin polymerization was analyzed by confocal microscopy, as described before.

Figure 8:
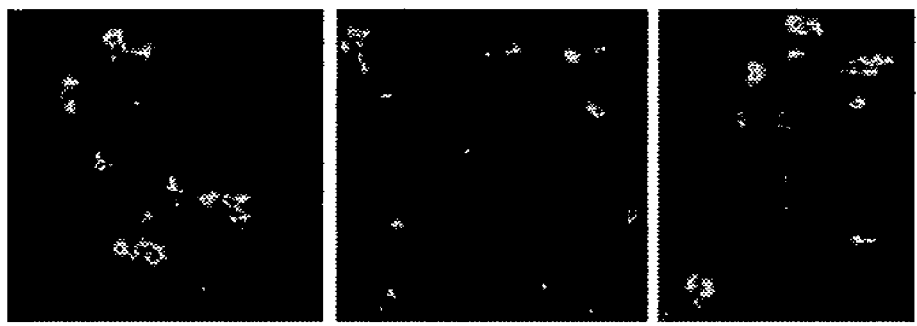
FIG. 8 illustrates the morphology of PC12-ES cells after treatment with either L-Bel1 (FIG. 8A), D-9rac (FIG. 8B) or peptide L-9K (FIG. 8C).
Figure 8:
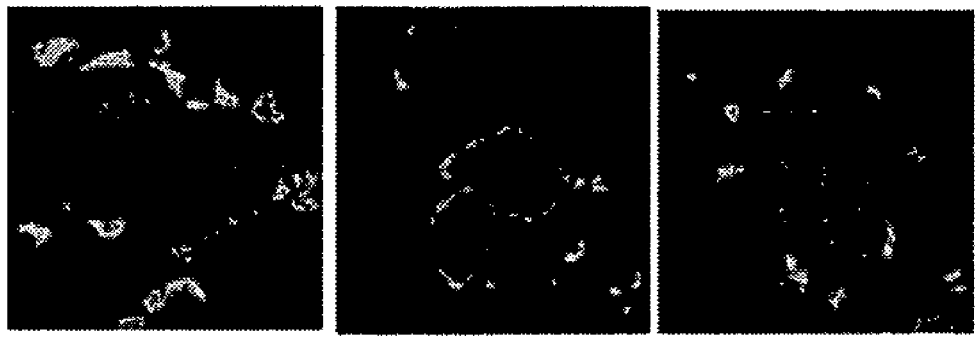
Figure 8:
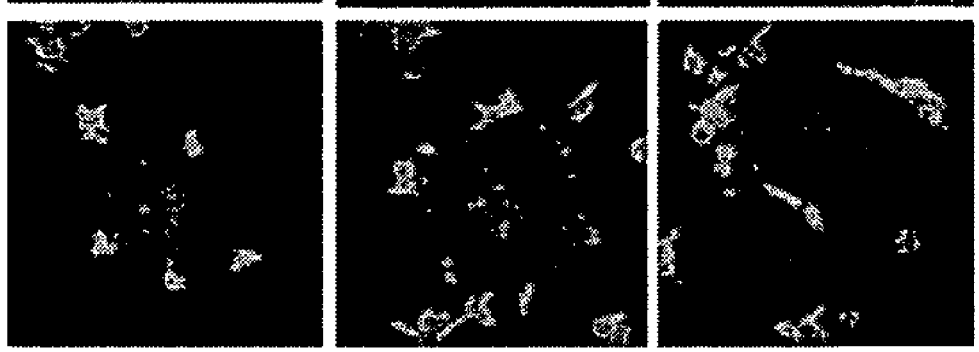

PC-12 cells treated with the peptides L-Bel1 and D-9Rac/am, labeled or unlabeled, at concentrations ranging from 2 to 10 µM, showed decreased actin content and organization, mainly at the focal adhesions (FIGS. 8A and 8B). The peptides appeared to induce morphological changes in treated cells, such as a more rounded cell shape (FIG. 8). The effect of both L-Bel1 and D-9Rac/am peptides on treated cells was comparable (FIGS. 8A and 8B). This effect suggested an induction of actin depolymerization (or blockage of actin polymerization) by the synthetic peptides. No effect was observed in non treated cells or in cells exposed to the peptide L-9K, where focal adhesions remained strongly stained. Nevertheless, at higher concentrations (100 µM), the described effect was almost lost, and cells showed a strong actin staining on their cellular processes. These results suggest that low concentrations of peptides L-Bel1 (SEQ ID NO. 3) and D-9Rac/am (SEQ ID NO. 15) are sufficient to promote actin reorganization.

Example 10

Effect of Peptides on Cellular Contraction

To study the effect(s) of the peptides on muscle cells, which associate with neurosecretory cells at neuromuscular junctions, peptides were cultured with rat lung fibroblast (LF) grown over wrinkling substrate (silicon) which can mimic the effects of contraction. These cells have a myofibroblastic phenotype, e.g., production of TGF-β, which make them suitable for cellular contraction/relaxation studies.

Wrinkling silicone substrates were prepared as essentially described previously (Harris, et al., *Science*. 208:177-179, 1980; Hinz, et al., *Mol Biol Cell*. 12:2730-41, 2001). Briefly, 50 µl of silicone (poly dimethyl siloxane; 30.000 centistokes, Dow Corning, Midland, Mich.) were deposited onto a 35 mm round glass coverslip at the bottom of a self-made observation chamber, which was centrifuged at 1.000 rpm for 2 minutes to spread the viscous fluid. The silicone surface was then crosslinked by passing it through a Bunsen flame; a flaming time of 1 second produced a surface stiffness that restricted wrinkle formation to fibroblasts with high contractile force (Hinz et al., supra). The polymerized silicone surface was finally coated with 10 µg/ml collagen type I (Sigma) for 2 hours at 37° C. Lung fibroblast cells were seeded at a density of 3.5×10³ cells/cm² and cultured for 1-2 days before the experiment.

Lung biopsy was obtained from a Sprague Dawley rat, divided in small tissue slices, placed in culture dishes, and maintained then in organ culture in Dulbecco's modified Eagle's medium (GibcoBRL, Life Technologie) containing 10% decomplemented fetal bovine serum (FBS) supplemented with 100 U/ml penicillin, 100 µg/ml streptomycin, 4 mM I-glutamine, at 37° C., in 5% $CO_2$. Cells were maintained during 2-3 weeks (2-8 passages), replacing medium frequently. At confluence, cells were detached from the culture dish with 0.125% trypsin-EDTA mixture (Sigma) for 10 minutes at 37° C., resuspended in complete medium, and seeded over silicon-coated tissue culture dishes at 3.5×10³ cells/cm². One to two days after, cells were treated with the appropriate peptide at 10 or 50 µM, and peptide-induced cell contraction/relaxation effect followed for 1-3 hours by live videomicroscopy. A smooth muscle cell line (A7r5) kept in similar conditions was also used to follow the peptide-induced effects on these cells grown over silicon sheet.

Live videomicroscopy was performed under controlled temperature and $CO_2$ conditions using a Zeiss Axiovert 200M (Zeiss, Oberkochem, Germany), equipped with a spinning disk Nipkow confocal head (Yokogawa CSU10), Photometrics CoolSNAP-HQ CCD camera and Metamorph 6.0 acquisition software (Visitron Systems, Puchheim, Germany). Phase contrast sequences were taken at a rate of 1 frame/10 sec using 10× (Plan-Neofluar, Ph1, NA 0.3) and 20× (Plan-Apochromat, Ph2, NA 0.5) Zeiss objectives.

A stressed collagen lattice contraction assay was also used to assess the effect of the peptides. For the contraction assay, lung fibroblasts were grown at 1.75×10⁵ cells/ml in mechanically restrained collagen lattices (1.0 mg/ml rat tail collagen 1, BD Biosciences) for 5 days as previously described (Hinz et al., supra). For contraction measurement, lattices were released using a syringe and lattice diameter was measured under dark-field illumination after 30 minutes. A minimum of 5 lattices was assessed per experimental condition, mean values were calculated and lattice diameter reduction was normalized to the lattice diameter before release (=% contraction). Peptides were added for 60 minutes before gel release.

Figure 9:
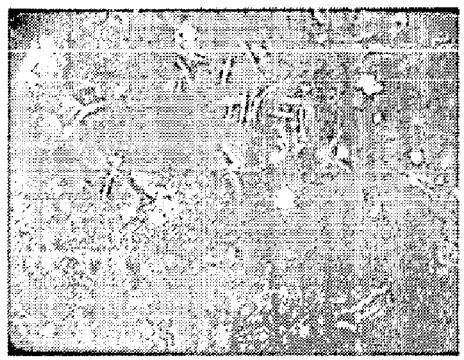
FIG. 9 depicts images of myofibroblast cells before (FIG. 9A) and after (FIG. 9B) treatment with peptide D-9Rac/am.
Figure 9:
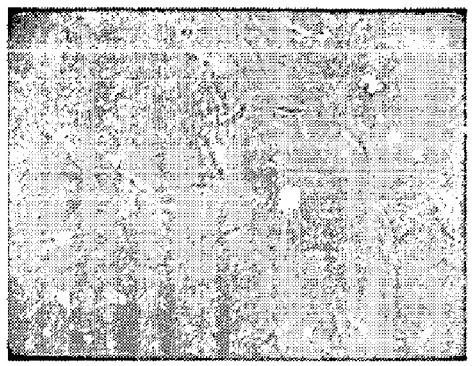

Lung myofibroblasts exposed to peptides L-Bel1 and D-9Rac/am (10 µM and 50 µM), showed a slow but constant loss of silicon substrate wrinkles and cell detachment, indicating a peptide-dependent relaxing effect on cells (FIGS. 9A and 9B). The same effect was observed on smooth muscle cells incubated with the same peptides. These effects were not observed on cells treated with the peptide L-9K. This peptide-induced cell relaxation is consistent with the lost of actin content on cellular processes observed on PC-12 cells treated with peptides L-Bel1 and D-9Rac/am. Decreased actin content and integrity on focal adhesions could contribute to cellular detachment from silicon substrate, changes in cell shape, and cell relaxation.

Figure 10:
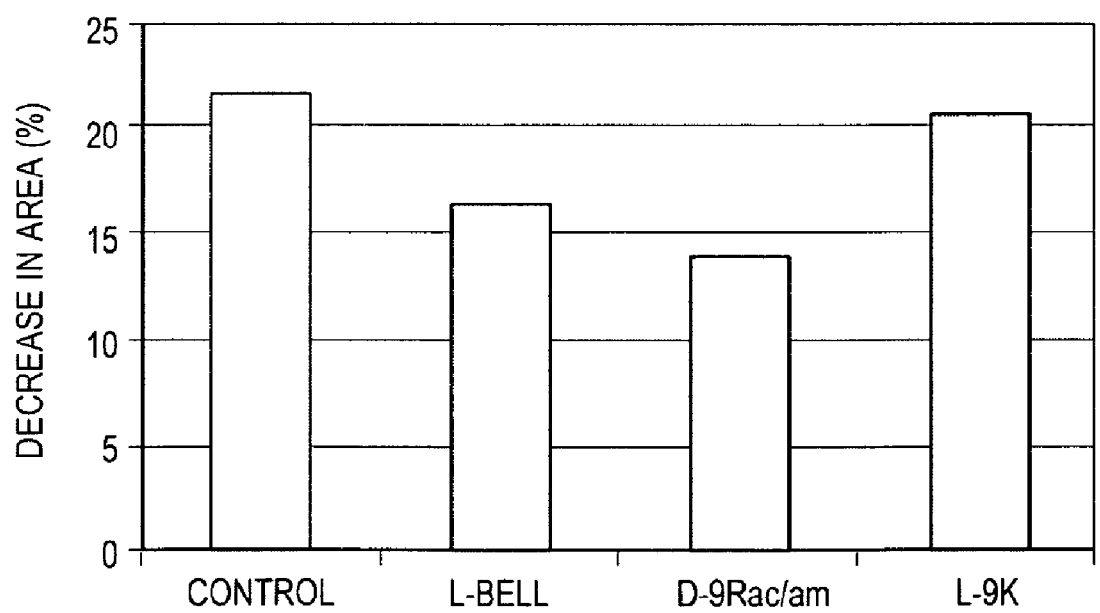
FIG. 10 describes the effects of peptides L-Bel-1, D-Rac/am, and L-9K on myofibroblast-mediated collagen contraction.

These results show a peptide-induced cell contraction/relaxation effect in a stressed collagen lattice contraction assay. Preliminary results showed a decrease in myofibroblast-mediated collagen gel contraction induce by the peptides L-Bel1 (SEQ ID NO. 3) and D-9Rac/am (SEQ ID NO. 15), compared to control gels (no peptide addition) and to L-9K (SEQ ID NO. 6) treated gels (FIG. 10).

This suggests that peptides L-Bel1 and D-9Rac/am induce cell relaxation, which correlates with the results related to actin filaments disclosed above.

Example 11

Administration of Peptide Composition

To determine the efficacy of the peptide composition of the invention in the treatment of facial wrinkles, clinical studies are performed. A peptide composition in emulsion as a cosmetic preparation is first tested in animal models to demonstrate a non toxic and non irritant effect. Initially, the integrity and stability of the peptide within the emulsion is controlled, as well as the possible modifications of the emulsifier (emulsifier's integrity). The emulsified peptides will than be tested for abnormal toxicity, dose dependent toxicity as well as for possible skin reactions in mouse and rabbits. Models for dermatological studies may be carried out using, preferably, a mammal, and more preferably, a human, cow, horse, cat, dog, pig, goat, sheep, rat, guinea pig, mouse, rabbit or other mammal suitable.

For example, the SCID-hu xenogeneic transplantation model (Boehncke W H *Arch Dermatol Res* 291:367-373, 1999) allows human grafts on immunodeficient SCID mice, which enables testing on human skin. An in vitro model for testing product on piglet cells is described in Wu et al. (*Br J Dermatol.* 152:1263-67, 2005) while Duval et al. (*Exp Dermatol.* 12 Suppl 2:64-70, 2003) describe an in vitro model for assessing cosmetics on human skin. Other models are well-known to those of skill in the art (e.g., Dreher et al., *Skin Pharmacol Appl Skin Physiol.* 15 Suppl 1:40-58, 2002).

After testing the peptide emulsion in animal models, the composition is administered to healthy volunteers. Skin topography analysis for measuring the effectiveness of the peptide composition is performed by first obtaining silicon imprints from the lateral preorbital region of healthy volunteers. An oil/water emulsion of the peptide is applied twice a day. Volunteers apply the emulsion containing the peptide in one lateral preorbital area, and the emulsion alone in the contra lateral side. Silicon imprints are obtained after 0, 15 and 30 days, and analyzed by confocal laser scanning microscopy to assess the evolution of the skin surface before and after treatment. Confocal microscopy in reflection mode and three-dimensional analysis to assess the different parameters of roughness is used. The same skin regions are selected before processing and after the processing (day 15 and day 30), by means of observation under magnifying glass with outer white light. The peptide effectively treats wrinkles if the results show modulation of the facial muscles, relaxes facial tension and reduces the depth of already formed wrinkles. An improvement in wrinkle depth of at least 30%, and from 30%-50% is considered a significant change in wrinkle depth.

Numerous modifications and variations in the invention as set forth in the above illustrative examples are expected to occur to those skilled in the art. Consequently only such limitations as appear in the appended claims should be placed on the invention.

What is claimed:

1. An isolated peptide comprising an amino acid sequence having at least 90% identity to SEQ ID NO:13.

2. The isolated peptide of claim 1, comprising an L amino acid.

3. The isolated peptide of claim 2, wherein the peptide is acetylated at the amino terminus.

4. The isolated peptide of claim 1 wherein the peptide is acetylated at the amino terminus.

5. An isolated peptide which is a retro-inverso isomer of the synthetic peptide of claim 1.

6. The isolated peptide of claim 1, wherein the peptide is a fusion protein.

7. The isolated peptide of claim 1, wherein the peptide is fused to a protein translocation domain.

8. The isolated peptide of claim 7, wherein the protein translocation domain is taken from the HIV TAT protein.

9. The isolated peptide of claim 7, wherein the protein translocation domain comprises a peptide having at least six contiguous amino acid residues that are L-arginine or D-arginine.

10. The isolated peptide of claim 7 wherein the protein translocation domain is a guanidino-rich sequence.

11. The isolated peptide of claim 1, wherein the peptide is fused to a nucleic acid.

12. The isolated peptide of claim 1, wherein the peptide is fused to the lipolytic peptide GKH.

13. A composition comprising the isolated peptide claim 1, wherein the composition is an oil in water emulsion.

14. A composition comprising the isolated peptide claim 1, wherein the composition is formulated for topical use.

15. A composition comprising the isolated peptide claim 1, wherein the total concentration of the peptide is from 0.00001% to 10% (w/w) of the total weight of the composition.

16. A composition of claim 15, wherein the total concentration of the peptide is about 0.001 to 1% (w/w) of the total weight of the composition.

17. A composition comprising the isolated peptide of claim 1, further comprising a neurotransmitter inhibitor.

18. The composition of claim 17, wherein the neurotransmitter inhibitor is selected from the group consisting of curare, a-bungarotoxin, gallamine, Pirenzepine AF-DX 116 pF-HHSiD, ipratroprium, scopolamine and atropine.

19. A composition comprising the isolated peptide of claim 1, further comprising a skin agent.

20. The composition of claim 19, wherein the skin agent is selected from the group consisting of a moisturizer, a depigmenting agent, a pro-pigmenting agent, a desquamating agent, a UV absorbing agent, a sunscreen active, a viscosity modifying agent, an abrasive agent, a pH adjustor, an antiglycation agent, an anti-oxidative agent, a NO-synthase inhibitor agent, an agent stimulating the synthesis of dermal macromolecules, an agent stimulating the synthesis of epidermal macromolecules, an agent preventing the degradation of dermal macromolecules, an agent preventing the degradation of epidermal macromolecules, an agent stimulating the synthesis of collagen, an agent preventing the degradation of collagen, an agent stimulating fibroblasts, an agent stimulating keratinocyte proliferation, an agent for stimulating keratinocyte differentiation, a muscle relaxant, a dermo relaxant, a rejuvenating agent, an anti-pollution agent, a free-radical scavenger, an agent acting on capillary circulation, an agent acting on the metabolism of cells, an anti-inflammatory agent, an anti-perspiring agent, an anti-microbial agent, an anti-fungal agent, an agent with adjuvant hydrophilic and lipophilic gel, an active agent, a preserving agent, a solvent, a fragrance, a filler, a pigment, and an odor absorber.

21. The isolated peptide of claim 1, wherein the peptide comprises SEQ ID NO: 13.

22. The isolated peptide of claim 1, consisting essentially of the amino acid sequence set forth in SEQ ID NO: 13.

23. An isolated peptide comprising an amino acid sequence having at least 85% identity to SEQ ID NO: 22 or SEQ ID NO: 23.

24. A method for improving tissue turgor comprising the step of topically contacting a cell with an effective amount of the isolated peptide of claim 1.

25. A method for inhibiting muscle contractions comprising the step of contacting a cell with an effective amount of the isolated peptide of any one of claim 1, wherein the contacting is performed by a route selected from the group consisting of transdermally, topically, intradermally, and subdermally.

26. A method for inhibiting neurotransmitter release comprising contacting a cell secreting neurotransmitters with an effective amount of the isolated peptide of claim 1, wherein the contacting is performed by a route selected from the group consisting of transdermally, topically, intradermally, and subdermally.

27. The method of claim 26 wherein the isolated peptide comprises L-amino acids.

28. A method for enhancing wound healing comprising the step of administering to a subject in need of wound healing an effective amount of the isolated peptide of claim 1.

29. A method for enhancing muscle repair comprising the step of administering to a subject in need of wound healing an effective amount of the isolated peptide of claim 1.

30. A method for blocking the fibrotic process in a wound comprising the step of administering to a subject in need of wound healing an effective amount of the isolated peptide of claim 1.

31. A method for treating disorders selected from the group consisting of hyperhidrosis, focal dystonia, nondystonic disorders, inflammation, and pain, comprising the step of administering to a subject in need an effective amount of the isolated peptide of claim 1, wherein the administering is performed by a route selected from the group consisting of transdermal, topical, intradermal, and subdermal.

32. A method for improving the appearance of the skin, the method comprising applying topically a cosmetic composition comprising the isolated peptide of claim 1 and a cosmetically acceptable vehicle.

33. The method according to claim 32, wherein said skin is aged, photoaged, dry, lined or wrinkled skin.

34. The method according to claim 33, wherein said composition further comprises an agent having skin benefit material.

35. The method according to claim 34, wherein said agent is selected from the group consisting of estradiol; progesterone; pregnanalone; coenzyme Q10; methylsolanomethane (MSM); copper peptide (copper extract); plankton extract (phytosome); glycolic acid; kojic acid; ascorbyl palmitate; all trans retinol; azaleic acid; salicylic acid; broparoestrol; estrone; adrostenedione; and androstanediols.

36. The method according to claim 32, wherein said composition further comprises a sunblock.

37. The method according to claim 32, wherein said cosmetically acceptable vehicle is an oil in water emulsion.

38. The method of claim 32, wherein said composition is selected from the group consisting of an emulsion, lotion, spray, aerosol, powder, ointment, cream and foam.

* * * * *

UNITED STATES PATENT AND TRADEMARK OFFICE
CERTIFICATE OF CORRECTION

PATENT NO. : 8,318,898 B2
APPLICATION NO. : 12/158775
DATED : November 27, 2012
INVENTOR(S) : Nicolas Fasel et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 749 days.

Signed and Sealed this
Fifteenth Day of October, 2013

Teresa Stanek Rea
*Deputy Director of the United States Patent and Trademark Office*

SEQUENCE LISTING

<160> NUMBER OF SEQ ID NOS: 29

<210> SEQ ID NO 1
<211> LENGTH: 33
<212> TYPE: PRT
<213> ORGANISM: Artificial sequence
<220> FEATURE:
<223> OTHER INFORMATION: Synthetic peptide: L-Tat-ESUP-A

<400> SEQUENCE: 1

Gly Tyr Gly Arg Lys Lys Arg Arg Gln Arg Arg Gly Ser Asn Lys
1               5                   10                  15

Thr Arg Ile Asp Glu Ala Asn Gln Arg Ala Thr Lys Met Leu Gly Ser
            20                  25                  30

Gly

<210> SEQ ID NO 2
<211> LENGTH: 22
<212> TYPE: PRT
<213> ORGANISM: Artificial sequence
<220> FEATURE:
<223> OTHER INFORMATION: Synthetic peptide: L-Tat-Argireline

<400> SEQUENCE: 2

Tyr Gly Arg Lys Lys Arg Arg Gln Arg Arg Gln Gly Ala Gly Gly
1               5                   10                  15

Glu Glu Met Gln Arg Arg
            20

<210> SEQ ID NO 3
<211> LENGTH: 13
<212> TYPE: PRT
<213> ORGANISM: Artificial sequence
<220> FEATURE:
<223> OTHER INFORMATION: Synthetic peptide: L-Tat

<400> SEQUENCE: 3

Gly Tyr Gly Arg Lys Lys Arg Arg Gln Arg Arg Arg Gly
1               5                   10

<210> SEQ ID NO 4
<211> LENGTH: 39
<212> TYPE: PRT
<213> ORGANISM: Artificial sequence
<220> FEATURE:
<223> OTHER INFORMATION: Synthetic peptide: L-Tat 49-86

<400> SEQUENCE: 4

Gly Arg Lys Lys Arg Arg Gln Arg Arg Arg Ala His Gln Asn Ser Gln
1               5                   10                  15

Thr His Gln Ala Ser Leu Ser Lys Gln Pro Thr Ser Gln Pro Arg Gly
            20                  25                  30

Asp Pro Thr Gly Lys Glu Gly
        35

<210> SEQ ID NO 5
<211> LENGTH: 13
<212> TYPE: PRT
<213> ORGANISM: Artificial sequence
<220> FEATURE:
<223> OTHER INFORMATION: Synthetic peptide: 9R-L

<400> SEQUENCE: 5

```
Gly Tyr Gly Arg Arg Arg Arg Arg Arg Arg Gly
1               5                   10

<210> SEQ ID NO 6
<211> LENGTH: 13
<212> TYPE: PRT
<213> ORGANISM: Artificial sequence
<220> FEATURE:
<223> OTHER INFORMATION: Synthetic peptide: 9K-L

<400> SEQUENCE: 6

Gly Tyr Gly Lys Lys Lys Lys Lys Lys Lys Lys Gly
1               5                   10

<210> SEQ ID NO 7
<211> LENGTH: 24
<212> TYPE: PRT
<213> ORGANISM: Artificial sequence
<220> FEATURE:
<223> OTHER INFORMATION: Synthetic peptide: MRPED

<400> SEQUENCE: 7

Lys Lys Lys Lys Lys Phe Ser Phe Lys Lys Pro Phe Lys Leu Ser Gly
1               5                   10                  15

Leu Ser Phe Lys Arg Asn Arg Lys
            20

<210> SEQ ID NO 8
<211> LENGTH: 24
<212> TYPE: PRT
<213> ORGANISM: Artificial sequence
<220> FEATURE:
<223> OTHER INFORMATION: Synthetic peptide: 3DMRPED

<400> SEQUENCE: 8

Lys Lys Lys Lys Lys Phe Asp Phe Lys Lys Pro Phe Lys Leu Asp Gly
1               5                   10                  15

Leu Asp Phe Lys Arg Asn Arg Lys
            20

<210> SEQ ID NO 9
<211> LENGTH: 37
<212> TYPE: PRT
<213> ORGANISM: Artificial sequence
<220> FEATURE:
<223> OTHER INFORMATION: Synthetic peptide: L-Tat-MRPED

<400> SEQUENCE: 9

Gly Tyr Gly Arg Lys Lys Arg Arg Gln Arg Arg Gly Lys Lys Lys
1               5                   10                  15

Lys Lys Phe Ser Phe Lys Lys Pro Phe Lys Leu Ser Gly Leu Ser Phe
                20                  25                  30

Lys Arg Asn Arg Lys
        35

<210> SEQ ID NO 10
<211> LENGTH: 37
<212> TYPE: PRT
<213> ORGANISM: Artificial sequence
<220> FEATURE:
<223> OTHER INFORMATION: Synthetic peptide: L-Tat-3DMRPED

<400> SEQUENCE: 10

Gly Tyr Gly Arg Lys Lys Arg Arg Gln Arg Arg Gly Lys Lys Lys
1               5                   10                  15
```

-continued

```
Lys Lys Phe Asp Phe Lys Lys Pro Phe Lys Leu Asp Gly Leu Asp Phe
                20                  25                  30
Lys Arg Asn Arg Lys
        35

<210> SEQ ID NO 11
<211> LENGTH: 13
<212> TYPE: PRT
<213> ORGANISM: Artificial sequence
<220> FEATURE:
<223> OTHER INFORMATION: Synthetic peptide: 9R-L-/Ac-am
<220> FEATURE:
<221> NAME/KEY: MISC_FEATURE
<222> LOCATION: (1)..(1)
<223> OTHER INFORMATION: Acetylation

<400> SEQUENCE: 11

Gly Tyr Gly Arg Arg Arg Arg Arg Arg Arg Arg Arg Gly
1               5                   10

<210> SEQ ID NO 12
<211> LENGTH: 13
<212> TYPE: PRT
<213> ORGANISM: Artificial sequence
<220> FEATURE:
<223> OTHER INFORMATION: Synthetic peptide: D-Tat
<220> FEATURE:
<221> NAME/KEY: misc_feature
<222> LOCATION: (1)..(13)
<223> OTHER INFORMATION: Corresponds to D-amino peptide "GYGRKKRRQR RRG"

<400> SEQUENCE: 12

Xaa Xaa Xaa Xaa Xaa Xaa Xaa Xaa Xaa Xaa Xaa Xaa Xaa
1               5                   10

<210> SEQ ID NO 13
<211> LENGTH: 13
<212> TYPE: PRT
<213> ORGANISM: Artificial sequence
<220> FEATURE:
<223> OTHER INFORMATION: Synthetic peptide: 9R-D
<220> FEATURE:
<221> NAME/KEY: misc_feature
<222> LOCATION: (1)..(13)
<223> OTHER INFORMATION: Corresponds to D-amino peptide "GYGRRRRRRR RRG"

<400> SEQUENCE: 13

Xaa Xaa Xaa Xaa Xaa Xaa Xaa Xaa Xaa Xaa Xaa Xaa Xaa
1               5                   10

<210> SEQ ID NO 14
<211> LENGTH: 13
<212> TYPE: PRT
<213> ORGANISM: Artificial sequence
<220> FEATURE:
<223> OTHER INFORMATION: Synthetic peptide: 9Rrev-D
<220> FEATURE:
<221> NAME/KEY: misc_feature
<222> LOCATION: (1)..(13)
<223> OTHER INFORMATION: Corresponds to D-amino peptide "GRRRRRRRRR GYG"

<400> SEQUENCE: 14

Xaa Xaa Xaa Xaa Xaa Xaa Xaa Xaa Xaa Xaa Xaa Xaa Xaa
1               5                   10

<210> SEQ ID NO 15
<211> LENGTH: 13
<212> TYPE: PRT
<213> ORGANISM: Artificial sequence
<220> FEATURE:
```

```
<223> OTHER INFORMATION: Synthetic peptide: 9R-D/Ac-am (D-9Rac/am)
<220> FEATURE:
<221> NAME/KEY: MISC_FEATURE
<222> LOCATION: (1)..(1)
<223> OTHER INFORMATION: Synthetic peptide: Acetylation
<220> FEATURE:
<221> NAME/KEY: misc_feature
<222> LOCATION: (1)..(13)
<223> OTHER INFORMATION: Corresponds to D-amino peptide "GYGRRRRRRR RRG"

<400> SEQUENCE: 15

Xaa Xaa Xaa Xaa Xaa Xaa Xaa Xaa Xaa Xaa Xaa Xaa Xaa
1               5                   10

<210> SEQ ID NO 16
<211> LENGTH: 7
<212> TYPE: PRT
<213> ORGANISM: Artificial sequence
<220> FEATURE:
<223> OTHER INFORMATION: Synthetic peptide: 3R

<400> SEQUENCE: 16

Gly Tyr Gly Arg Arg Arg Gly
1               5

<210> SEQ ID NO 17
<211> LENGTH: 8
<212> TYPE: PRT
<213> ORGANISM: Artificial sequence
<220> FEATURE:
<223> OTHER INFORMATION: Synthetic peptide: 4R

<400> SEQUENCE: 17

Gly Tyr Gly Arg Arg Arg Arg Gly
1               5

<210> SEQ ID NO 18
<211> LENGTH: 9
<212> TYPE: PRT
<213> ORGANISM: Artificial sequence
<220> FEATURE:
<223> OTHER INFORMATION: Synthetic peptide: 5R

<400> SEQUENCE: 18

Gly Tyr Gly Arg Arg Arg Arg Arg Gly
1               5

<210> SEQ ID NO 19
<211> LENGTH: 10
<212> TYPE: PRT
<213> ORGANISM: Artificial sequence
<220> FEATURE:
<223> OTHER INFORMATION: Synthetic peptide: 6R
<220> FEATURE:
<221> NAME/KEY: misc_feature
<222> LOCATION: (1)..(10)
<223> OTHER INFORMATION: Corresponds to D-amino peptide "GYGRRRRRRG"

<400> SEQUENCE: 19

Xaa Xaa Xaa Xaa Xaa Xaa Xaa Xaa Xaa Xaa
1               5                   10

<210> SEQ ID NO 20
<211> LENGTH: 11
<212> TYPE: PRT
<213> ORGANISM: Artificial sequence
<220> FEATURE:
<223> OTHER INFORMATION: Synthetic peptide: 7R

<400> SEQUENCE: 20
```

```
Gly Tyr Gly Arg Arg Arg Arg Arg Arg Gly
1               5                   10
```

<210> SEQ ID NO 21
<211> LENGTH: 12
<212> TYPE: PRT
<213> ORGANISM: Artificial sequence
<220> FEATURE:
<223> OTHER INFORMATION: Synthetic peptide: 8R

<400> SEQUENCE: 21

```
Gly Tyr Gly Arg Arg Arg Arg Arg Arg Arg Gly
1               5                   10
```

<210> SEQ ID NO 22
<211> LENGTH: 38
<212> TYPE: PRT
<213> ORGANISM: Artificial sequence
<220> FEATURE:
<223> OTHER INFORMATION: Synthetic peptide: 9R-MRP

<400> SEQUENCE: 22

```
Gly Tyr Gly Arg Arg Arg Arg Arg Arg Arg Arg Gly Lys Lys Lys
1               5                   10                  15

Lys Lys Lys Phe Ser Phe Lys Lys Pro Phe Lys Leu Ser Gly Leu Ser
            20                  25                  30

Phe Lys Arg Asn Arg Lys
        35
```

<210> SEQ ID NO 23
<211> LENGTH: 19
<212> TYPE: PRT
<213> ORGANISM: Artificial sequence
<220> FEATURE:
<223> OTHER INFORMATION: Synthetic peptide: 9R-D Argireline
<220> FEATURE:
<221> NAME/KEY: misc_feature
<222> LOCATION: (1)..(19)
<223> OTHER INFORMATION: Corresponds to D-amino peptide "GYGRRRRRR
      RRGEEMQRR"

<400> SEQUENCE: 23

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa
```

<210> SEQ ID NO 24
<211> LENGTH: 6
<212> TYPE: PRT
<213> ORGANISM: Artificial Sequence
<220> FEATURE:
<223> OTHER INFORMATION: Synthetic peptide

<400> SEQUENCE: 24

```
Glu Glu Met Gln Arg Arg
1               5
```

<210> SEQ ID NO 25
<211> LENGTH: 5
<212> TYPE: PRT
<213> ORGANISM: Artificial Sequence
<220> FEATURE:
<223> OTHER INFORMATION: Synthetic peptide

<400> SEQUENCE: 25

```
Lys Lys Thr Thr Ser
```

```
<210> SEQ ID NO 26
<211> LENGTH: 5
<212> TYPE: PRT
<213> ORGANISM: Artificial Sequence
<220> FEATURE:
<223> OTHER INFORMATION: Synthetic peptide

<400> SEQUENCE: 26

Lys Thr Thr Lys Ser
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic peptide

<400> SEQUENCE: 27

Ala Gly Gly Glu Glu Met Gln Arg Arg
1               5

<210> SEQ ID NO 28
<211> LENGTH: 17
<212> TYPE: PRT
<213> ORGANISM: Artificial Sequence
<220> FEATURE:
<223> OTHER INFORMATION: Synthetic peptide

<400> SEQUENCE: 28

Ser Ala Ala Glu Ala Phe Ala Lys Leu Tyr Ala Glu Ala Phe Ala Lys
1               5                   10                  15

Gly

<210> SEQ ID NO 29
<211> LENGTH: 20
<212> TYPE: PRT
<213> ORGANISM: Artificial Sequence
<220> FEATURE:
<223> OTHER INFORMATION: Synthetic peptide

<400> SEQUENCE: 29

Ser Asn Lys Thr Arg Ile Asp Glu Ala Asn Gln Arg Ala Thr Lys Met
1               5                   10                  15

Leu Gly Ser Gly
            20
```